(12) United States Patent
Arlagadda et al.

(10) Patent No.: US 12,315,620 B2
(45) Date of Patent: May 27, 2025

(54) ENHANCED ENTERPRISE IMAGE READING WITH SEARCH AND DIRECT STREAMING

(71) Applicant: GE Precision Healthcare, LLC, Wauwatosa, WI (US)

(72) Inventors: Vijay Kumar Arlagadda, Hoffman Estates, IL (US); Yik Chi Benjamin Cheung, Naperville, IL (US); Andrew C. Holder, Crystal Lake, IL (US); Mukesh Jain, Hoffman Estates, IL (US); Arun Viswanath, Barrington, IL (US); Ashish D. Vassa, Lake Zurich, IL (US); Oleg Ledeniov, Glen Rock, NJ (US); Chandrakanth Murgkar, Aurora, IL (US); Garrett Rogers, Channahon, IL (US); Kush Thakker, Streamwood, IL (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 554 days.

(21) Appl. No.: 17/105,825

(22) Filed: Nov. 27, 2020

(65) Prior Publication Data
US 2021/0158938 A1    May 27, 2021

Related U.S. Application Data

(60) Provisional application No. 62/941,263, filed on Nov. 27, 2019.

(51) Int. Cl.
G16H 30/40    (2018.01)
G16H 10/60    (2018.01)

(52) U.S. Cl.
CPC ............. *G16H 30/40* (2018.01); *G16H 10/60* (2018.01)

(58) Field of Classification Search
None
See application file for complete search history.

(56) References Cited

U.S. PATENT DOCUMENTS 10,243,788 B1 *   3/2019   White ................. H04L 41/0806
10,432,648 B1 *  10/2019   Xu ....................... H04L 63/1416
11,688,495 B2 *   6/2023   De Francesco ........ G16H 10/60
                                                     713/182

(Continued)

OTHER PUBLICATIONS

Lauro et. al., Digital Pathology Consultations—a New Era in Digital Imaging, Challenges and Practical Applications, J Digit Imaging 26:668-677, 2013 (Year: 2013).*

*Primary Examiner* — Anne-Marie K Alderson

(57) ABSTRACT

Systems, apparatus, instructions, and methods for enterprise reading with search and streaming of information from local and remote sources are disclosed. An example apparatus includes a viewer to generate a request for patient content and to display at least a subset of the patient content according to a hanging protocol. The example apparatus includes a search service to query a plurality of sources for the patient content based on a patient identifier. The example query is to return meta data to generate at least one token encapsulating a location of identified patient content and an indication of access to the identified patient content. The example apparatus includes a streaming service to obtain the identified patient content using the at least one token and to provide the identified patient content to the viewer for display.

20 Claims, 19 Drawing Sheets

(56) References Cited

U.S. PATENT DOCUMENTS

| | | | |
|---|---|---|---|
| 2009/0249125 A1* | 10/2009 | Bhatawdekar | H04L 51/00 |
| | | | 714/39 |
| 2010/0215232 A1* | 8/2010 | Woo | G16H 20/40 |
| | | | 382/305 |
| 2011/0213774 A1* | 9/2011 | Buurman | G16H 10/60 |
| | | | 707/E17.019 |
| 2011/0231921 A1* | 9/2011 | Narayanan | G06F 21/335 |
| | | | 726/9 |
| 2013/0166767 A1 | 6/2013 | Olivier | |
| 2015/0149209 A1* | 5/2015 | Raizada | G16H 10/60 |
| | | | 705/3 |
| 2016/0092551 A1* | 3/2016 | Tang | G06F 16/313 |
| | | | 707/740 |
| 2016/0119582 A1* | 4/2016 | Smurro | G16H 80/00 |
| | | | 348/14.08 |
| 2016/0156630 A1* | 6/2016 | Raizada | G16H 30/20 |
| | | | 726/4 |
| 2018/0198795 A1 | 7/2018 | Raizada | |
| 2018/0329609 A1* | 11/2018 | De Swarte | G06T 19/00 |
| 2019/0180862 A1* | 6/2019 | Wisser | G16H 80/00 |
| 2020/0043167 A1* | 2/2020 | Murayama | G16H 30/40 |
| 2020/0082930 A1* | 3/2020 | De Francesco | G16H 10/60 |
| 2020/0153827 A1* | 5/2020 | Moen | H04L 63/1441 |
| 2021/0391040 A1* | 12/2021 | Dormer | G16H 10/20 |

* cited by examiner

| Centricity Universal Viewer | | | | Boss, Jack | 🔍 ▾ | 🔍 MRN / Patient ID | 🔍 Accession Number | 🔍 7 ▾ | ⓘ | WEBDXUSER ▾ |
|---|---|---|---|---|---|---|---|---|---|---|
| SPLIT SCREEN | | | FULL SCREEN | | | | | | | |
| PATIENT NAME SEARCH RESULTS | | | | | | | | | | |
| Boss, Jack | | | | | | | | | | |
| MENU | < Back to Previous Worklists | | | | | | | | | |
| Pin worklists here | All Dates | | | | ALL ④ | | | | | |
| | ⓧ | CT | 11:00AM 08/09/2019 CTANGHEAD DEMO | Boss, Jack | | DOB 12/03/2008 | Unassigned FVATU | | MRN Jack002 Acc No Ac10718969458O1 | UNKNOWN No information available |
| | ⓧ | CT | 11:00AM 08/09/2019 CTANGHEAD DEMO | Boss, Jack | | DOB 12/03/2008 | Unassigned FVATU | | MRN Jack002 Acc No Ac10718969458O1 | UNKNOWN No information available |
| | ⓧ | CT | 11:00AM 08/09/2019 CTANGHEAD DEMO | Boss, Jack | | DOB 12/03/2008 | Unassigned FVATU | | MRN Jack002 Acc No Ac10718969458O1 | UNKNOWN No information available |
| | ⓧ | CT | 11:00AM 08/09/2019 CTANGHEAD DEMO | Boss, Jack | | DOB 12/03/2008 | Unassigned FVATU | | MRN Jack002 Acc No Ac10718969458O1 | UNKNOWN No information available |

| Navigator | | | | | | | |
|---|---|---|---|---|---|---|---|
| < Study Selector | | | | | | | |
| ⦿ All Exams ◯ Relevant | | | | | | | |
| ☑ All ☐ CT | | | | | | | |
| Status | Rpt | Data | Time | Modality | Description | Remote Institution | Ser/Img |
| | | Sep-12-2019 | 11:00:00 AM | CT | CTANGHEAD DEMO | Repo_Provider_54 | 16/506 |
| | | Sep-11-2019 | 11:00:00 AM | CT | CTANGHEAD DEMO | Repo_Provider_54 | 2/506 |
| | | Sep-10-2019 | 11:00:00 AM | CT | CTANGHEAD DEMO | Repo_Provider_54 | 2/506 |
| | | Sep-09-2019 | 11:00:00 AM | CT | CTANGHEAD DEMO | Repo_Provider_54 | 2/506 |

ENHANCED ENTERPRISE IMAGE READING WITH SEARCH AND DIRECT STREAMING

CROSS-REFERENCE TO RELATED APPLICATION

This patent claims priority to U.S. Provisional Application Ser. No. 62/941,263, entitled "Enhanced Enterprise Image Reading with Search and Direct Streaming" which was filed on Nov. 27, 2019, and is hereby incorporated herein by reference in its entirety.

FIELD OF THE DISCLOSURE

This disclosure relates generally to enterprise healthcare processing and, more particularly, to enterprise healthcare processing and associated methods including image reading with search and direct streaming.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example. A wealth of information is available, but the information can be siloed in various separate systems requiring separate access, search, and retrieval. Correlations between healthcare data remain elusive due to technological limitations on the associated systems. Additionally, access between different healthcare systems remains disconnected, unpredictable, and problematic.

BRIEF SUMMARY

Certain examples provide an apparatus for cross-enterprise image reading. The example apparatus includes a viewer to generate a request for patient content and to display at least a subset of the patient content according to a hanging protocol. The example apparatus includes a search service to query a plurality of sources for the patient content based on a patient identifier. The example query is to return meta data to generate at least one token encapsulating a location of identified patient content and an indication of access to the identified patient content. The example apparatus includes a streaming service to obtain the identified patient content using the at least one token and to provide the identified patient content to the viewer for display.

Certain examples provide a computer-implemented method of cross-enterprise image reading. The example method includes querying, by executing an instruction using at least one processor, a plurality of sources for patient content based on a patient identifier. The example method includes generating, by executing an instruction using the at least one processor, at least one token encapsulating a location of identified patient content and an indication of access to the identified patient content based on meta data returned in response to the query. The example method includes obtaining, by executing an instruction using the at least one processor, the identified patient content using the at least one token. The example method includes providing, by executing an instruction using the at least one processor, the identified patient content for display via a viewer in response to a request.

Certain examples provide at least one computer readable storage medium comprising instructions that, when executed, cause at least one processor to at least: query a plurality of sources for patient content based on a patient identifier; generate at least one token encapsulating a location of identified patient content and an indication of access to the identified patient content based on meta data returned in response to the query; obtain the identified patient content using the at least one token; and provide the identified patient content for display via a viewer in response to a request.

BRIEF DESCRIPTION OF DRAWINGS

FIGS. 8-12 illustrate example graphical user interfaces that can be generated using the example systems of FIGS. 1-7B.

DETAILED DESCRIPTION OF CERTAIN EMBODIMENTS

Figure 1:
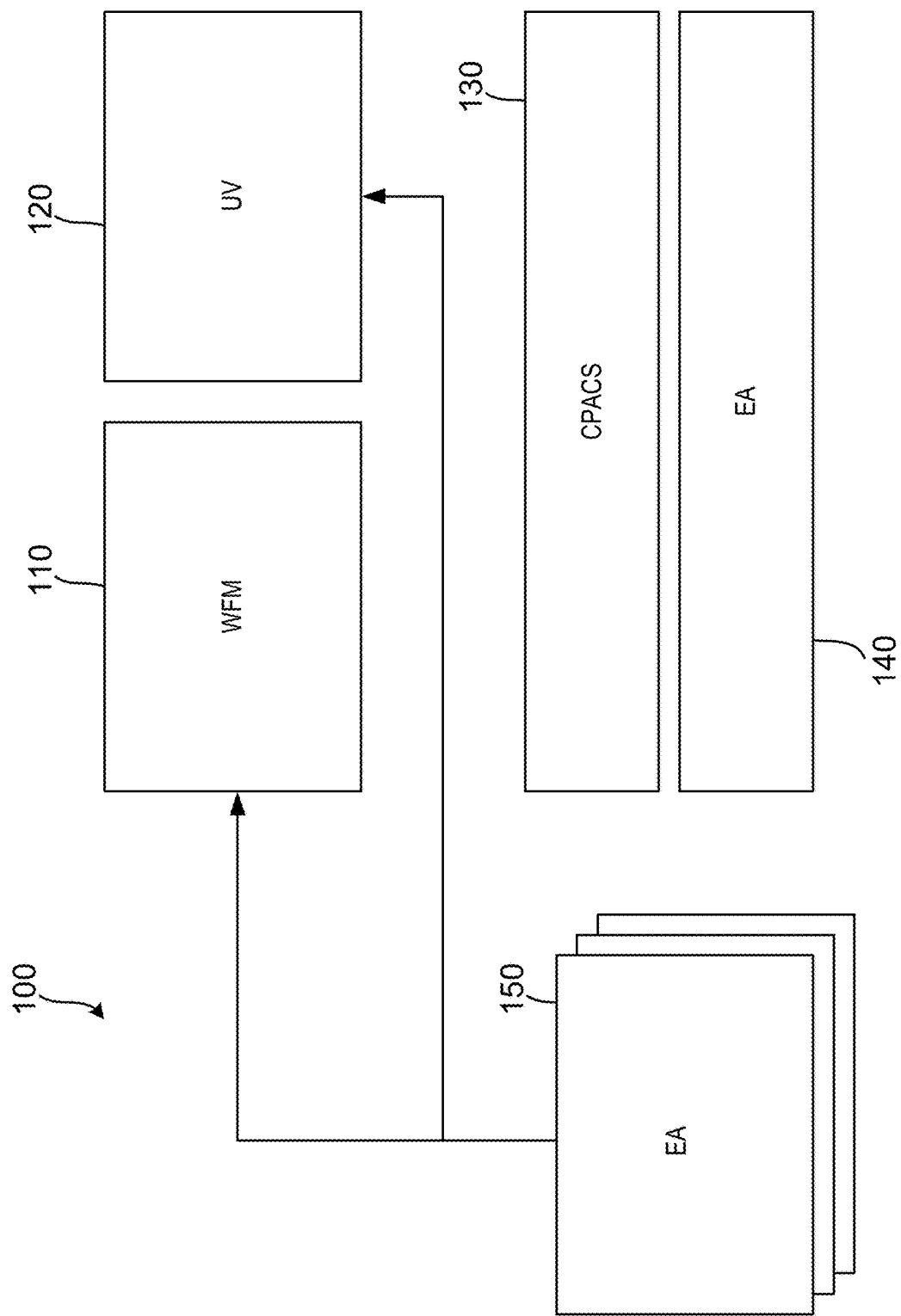
FIGS. 1-6 illustrate example system configurations for local and/or remote image/exam searching, streaming, and analysis.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects, and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities, and/or steps, the phrase "at least one of A or B" is intended to refer to implementations including any of (1) at least one A, (2) at least one B, and (3) at least one A and at least one B.

In addition, it should be understood that references to "one embodiment" or "an embodiment" of the present disclosure are not intended to be interpreted as excluding the existence of additional embodiments that also incorporate the recited features.

Many healthcare environments include radiology information systems to facilitate patient examination and/or patient diagnosis. For example, a radiology information system in a healthcare system can store radiology reports, messages, warning, alerts, patient scheduling information, patient demographic data, patient tracking information, and/or physician and patient status monitors.

Typically, a medical exam ordered for a patient is assigned to a practitioner (e.g., a radiologist) to conduct the exam. A medical exam conducted on a patient can involve review by a healthcare practitioner (e.g., a radiologist) to obtain, for example, diagnostic information from the exam. In a hospital setting, medical exams can be ordered for a plurality of patients, all of which involve review by an examining practitioner. Each exam may have associated attributes, such as a modality, a part of the human body under exam, and/or an exam priority level related to a patient criticality level. In some examples, however, not all the information needed for reviewing a medical exam is locally available. For example, a practitioner (e.g., a radiologist or a technician) may want to review information about a patient, but the information may be spread across different information systems.

In some systems, the practitioner can review printouts of the information from the different information systems. However, the printouts may not include up-to-date information. For example, information in an information system may be updated to include a new resting heart rate for the patient. In some systems, the practitioner can access the information from the different information systems by manually connecting to each of the necessary information systems. This cumbersome process of logging into an information system whenever information from that information system is needed can cause the practitioner to obtain the information less frequently. Thus, the practitioner may end up reviewing the medical exam (or record) for the patient with stale and/or incomplete information.

In some systems, a healthcare institution builds a unified system that includes all the data from the different information systems. For example, the unified system can populate the unified system with all the information stored in a first hospital information system, a second hospital information system, a radiology information system, etc. Such unified systems necessitate large databases to store all of the information. Further, transforming the information (e.g., cleansing, reformatting, standardizing, aggregating and/or applying any number of business rules) from the different information systems into a single format as needed for the unified system can be impractical. For example, each of the different information systems can be controlled by different business rules or service level agreements, store the information in different formats, include different definitions for optional elements versus required elements, etc. In addition, if the information is transformed at the unified system, returning the data (e.g., information updated by the practitioner) to the source information system can be unreasonable.

In other cases, disparate systems, rather than a unified system, are used to provide patient information, diagnosis, and treatment. Certain examples provide a "bolt-on approach" allowing for immediate use of existing data by the new application without synchronization. Certain examples use Extract, Transform, Load (ETL) to extract data from outside sources, transform the extracted data to fit operational needs, and load the transformed data into an end target data store. Certain examples reduce install/upgrade time and service costs by reducing or eliminating ETL in accordance with a single schema. The schema is a structure described according to a language and/or other format to provide one or more formula, format, integrity constraint, relationship, attribute, rule, etc., to organize, relate, process, and/or store information. Certain examples facilitate these operations via the new application while the existing base application continues to function as before, oblivious to another (e.g., competing) application (e.g., the "new" application) working on the same schema/dataset. This allows customers to slowly transition from an existing application to the new and different application while not suffering from data migration to do so.

In certain examples, a HIS stores medical information such as clinical reports, patient information, and/or administrative information received from, for example, personnel at a hospital, clinic, and/or a physician's office. A RIS stores information such as radiology reports, radiology exam image data, messages, warnings, alerts, patient scheduling information, patient demographic data, patient tracking information, and/or physician and patient status monitors. Additionally, the MS enables exam order entry (e.g., ordering an x-ray of a patient) and image and film tracking (e.g., tracking identities of one or more people that have checked out a film). In some examples, information in the RIS is formatted according to the HL-7 (Health Level Seven) clinical communication protocol. In certain examples, a medical exam distributor is located in the RIS to facilitate distribution of radiology exams to a radiologist workload for review. In an alternative example, the exam distributor can be located separately or can be included in any other suitable device of the healthcare system.

A PACS stores medical images (e.g., x-rays, scans, three-dimensional renderings, etc.) as, for example, digital images in a database or registry. In some examples, the medical images are stored in the PACS using the Digital Imaging and Communications in Medicine ("DICOM") format. Images are stored in the PACS by healthcare practitioners (e.g., imaging technicians, physicians, radiologists) after a medical imaging of a patient and/or are automatically transmitted from medical imaging devices to the PACS for storage. In some examples, the PACS can also include a display device and/or viewing workstation to enable a healthcare practitioner or provider to communicate with the PACS.

Diagnostic and medical image processing solutions such as PACS and RIS help to drive and support digital images and patient data through improved image storage, viewing, sharing and retrieval, resulting in an improvement in workflow efficiency and productivity. Such improvements are of growing importance as the world population ages and co-morbidities increase demand for medical imaging and analytics and a resulting need for image processing and management for large volumes of data.

Additionally, PACS have evolved from a tool for medical image viewing, distribution, and archiving into a system supporting clinical decision making. PACS can include advanced visualization tools, voice recognition solutions, customized worklists, teleradiology, cloud-based PACS, zero-footprint viewers, and mobile PACS, for example. PACS may be integrated with three-dimensional (3D) 3D visualization, maximum intensity projection (MIP), and multi-planar reformation (MPR) tools, for example.

In certain examples, a Vendor-Neutral Archive (VNA) can be used in place of and/or in addition to a PACS for image archiving and/or other storage. Using a VNA, a plurality of different PACS and/or other different systems can store and retrieve images without translation or transformation at the VNA. An enterprise archive (EA) can also be used within an enterprise to storage and later retrieve image and/or other data, for example.

In certain examples, one or more integrated systems can be provided and/or can communicate across multiple healthcare enterprises. Certain examples provide cross-enterprise or supra-enterprise communication, collaboration, and information sharing to provide access but retain ownership and/or control of data. For example, an entity's workload can be shared across competitors while enabling that entity to retain control of its customer base but still provide access to (but retain control over) relevant records. In some examples, collaboration may be facilitated between different legal entities with different systems, for example. In certain examples, a user from a local system trying to access data and/or functionality from a remote system can be authenticated by the local system and authorized by the remote system.

A plurality of configurations can be implemented for cross-enterprise communication and collaboration with an integrated clinical system. Various designs can be configured to help satisfy one or more metrics including serviceability (e.g., installability, upgradability, break/fix workflows, etc.), performance (e.g., throughput, latency, high availability, scalability, etc.), security, usability, product development, and marketability, for example.

Certain examples support cross-enterprise informational constructs such as a single global patient jacket across multiple institutions, a global reading worklist for a radiologist, etc., as well as facilitating reporting into a system from which an exam being read originated. Certain examples facilitate cross-enterprise interaction without a common master file across participating enterprises (but with, for example, a master patient index (MPI)) and without data duplication (e.g., a single system of record).

In certain examples, a cross-enterprise arrangement is decentralized to allow participants to allow and/or restrict people, requests, etc., according to one or more "local" rules, procedures, preferences, etc. A user's local system can be responsible for authentication (is this user who he claims to be?), while a target local and/or remote system may be responsible for authorization (does this user have an ability to do X-Y-Z in my system?). In this way, existing enterprise organizations can be leveraged into a cross-enterprise framework without further change.

For example, a trusted enterprise can reach out to a local machine, and its agent can verify that a user from the trusted enterprise has access. For example, this user is from enterprise A, and this user wants to access certain images from a machine in enterprise C. Enterprise A authenticates the user, and enterprise C authorizes the access (access control is in the hands of enterprise C). Thus, certain examples facilitate authentication of a user at the remote "home" system for the user but authorize access for the user locally at the system in question. By allowing each user's system to handle authentication and each data/application's system to handle authorization for access to its application/data, certain examples allow for multi-technology users (e.g., different and competing technology stacks can be used together) and cross-application communication.

Further, certain examples facilitate easy transitions for enterprises coming into or going out of cross-enterprise sharing. For example, a user in enterprise A does not need to know anything about users in enterprise C. Enterprise A can set its own rules about users and can revoke and/or change rules, users, etc., at any time without interference from another enterprise. If enterprise C leaves the collaboration, then enterprise C can shut down the external trust previously given to enterprise A and other collaborating enterprises so that enterprise C then treats those enterprises as if it does not know them.

Certain examples help reduce implementation time and complexity (e.g., an implementation time of zero) by leveraging existing infrastructure and/or capability (e.g., LDAP authentication mechanism already built in to local enterprise) versus a centralized authentication/authorization approach (which requires enterprises to maintain their list of users both locally and with respect to the central server). With a centralized approach, if a user is disabled locally but not centrally, that user still has access as far as the central authority is concerned; with decentralized collaboration, the user has to ask the local enterprise.

In certain examples, radiology tasks can be organized in a single, intelligent workflow to collaboratively deliver more efficient patient care and improved utilization of imaging resources. Certain examples facilitate automatic prioritization of studies across an enterprise based on a radiologist worklist, based on the skill, sub-specialty, experience and service level agreements, and so on. Certain examples help to enhance virtual collaboration between radiologists, referring physicians, and other specialists to improve confidence in diagnostic findings. Certain examples enable distributed radiologists to share reading workload for studies performed at other locations. Certain examples provide a workflow-enabled, comprehensive solution to image management, reporting, and analytics to help drive patient care. Certain examples provide native tag morphing to optimize or otherwise improve image sharing and workflows via a diagnostic viewer. Certain examples facilitate enterprise and community wide collaboration (e.g., via a cloud-based and/or other server-based infrastructure, etc.).

In certain examples, primary and/or comparison studies can be searched and streamed across a distributed enterprise from a single application/single viewer (e.g., a Universal viewer, a zero footprint viewer, another enterprise viewer, imaging desktop, radiology desktop, etc.) while maintaining radiologist preferences, other hanging protocol settings (e.g., Smart Hanging Protocols, Smart Reading Protocols, etc.), etc., without performing time-consuming data migrations or impacting system settings without authorization. Certain examples provide a workflow and associated apparatus providing distributed searching function and real-time (or substantially real-time given data transmission, processing, storage, and/or retrieval latency) streaming to support study reading across a distributed enterprise.

Certain examples enable a user to search a patient's study across a healthcare enterprise network. Certain examples enable a user to ready the study across the enterprise. Certain examples reduce or eliminate error-prone manual processing in daily clinician workflow. Certain examples improve time to care. Certain examples remove location restriction and enable centralized reading, annotation, processing, etc.

An enterprise-wide patient information search addresses technical problems in image/exam searching, exam reading, etc., such as correctly identifying patient identity, resolving duplicate information result sets, etc. Certain examples provide a system wide generic standard information model (e.g., as an application programming interface or API, etc.) to support data retrieval from different archive equipment. Certain examples provide concurrent data processing to resolve performance and scalability problems.

Streaming study meta data and pixel information allows a system to retrieve/receive meta data and stream pixel data to a viewer. Such a service enables retrieval of meta data from different archives that cross over network boundaries. Certain examples enable pixel data to be streamed at a specific priority between viewer and archive. The viewer can indicate image state, and streaming priority can be adjusted as appropriate/warranted/desired, for example.

Certain examples allow a user, program, system, device, etc., to search across an enterprise and/or across enterprises and launch a local viewer for a primary remote exam. This is useful in a multi-PACS environment in which one user in a site (Site A) might want to see an exam in another site (Site B), for example.

Additionally, a local viewer can be launched to stream content directly from a third-party PACS, a remote EA, a third party VNA, etc., while seamlessly hanging primary and comparison exams according to users preferred hanging protocol, smart reading protocol, etc., irrespective of a source of the exam. Access is provided to DICOM artifacts for a remote exam including Greyscale Softcopy Presentation States (GSPS), key image notes (KIN), etc., and a resulting report can be stored as a structured report (e.g., a DICOM Basic Text SR, etc.) to search across an enterprise and launch a local viewer for a primary remote exam, for example.

Certain examples enable viewing of migrated exams from an adopted archive without prefetching to a local PACS. Migrated exams can be directly streamed from the adopted archive without a user-initiated fetch to the local PACS, for example. Archive adopted studies can be seamlessly hung as primary and/or comparison exams using a preferred hanging protocol, smart reading protocol, etc., with access to KIN, GSPS, etc.

Thus, in an enterprise environment, there are multiple PACS systems, and a patient's data can be located in one or more different locations, systems, etc. To view, read, etc., all the studies of a patient or set of patients, current users and systems must manually move all the studies into a single PACS. Such a process can take hours, or even days, and is error-prone, while a patient awaits diagnosis and treatment for potentially life-threatening conditions. Instead, certain examples provide searching to locate patient study(-ies) in multiple PACS and/or other storage, as well as direct streaming of study(-ies) to a local viewer application.

FIGS. 1-6 illustrate a plurality of system configurations to enable interaction, retrieval, and display of information between a local site and a remote site. Various configurations can be dynamically determined based on one or more factors such as access restrictions, availability of information, user/administrator preference, timing, requesting system, etc. In certain examples, one or more client viewers can access a remote repository through a common, local proxy. Data communication occurs through a common channel from the locate site to the remote site. For example, the common channel can be implemented using a high speed network to provide improved responsiveness and improved security over prior connections.

In certain examples, one or more remote studies can be prefetched to a local system. If images are located in an archive beyond a remote enterprise archive or a central device, the prefetch can occur on a remote device, which can then communicate the retrieved image study to a local archive.

In certain examples, retrieved image data is not imported into local storage, and changes are made remotely at the source rather than at the local viewing system. In certain examples, files are modified, created, etc., at the remote source location, rather than the local viewing location. A site-level permission and/or other access criterion can determine whether a system, user, etc., is allowed to change a file, create a new file, etc., at the remote system, for example.

FIG. 1 illustrates an example system 100 in which a remote primary exam is to be read at a local site. As shown in the example of FIG. 1, a local site includes a workflow manager 110, a diagnostic viewer 120, a PACS 130, and an EA 140. A remote site includes another EA 150. The workflow manager 110 can search the remote archive(s) 150 by patient demographic, study detail, etc., to retrieve an image/exam for display and interaction via the local viewer 120, for example. The primary study from the remote EA 150 can be launched in the viewer 120 directly from the remote archive(s) 150. Searching and streaming can be provided to the local viewer 120 from multiple remote archives 150, for example.

Thus, for example, if hospital A buys hospital B, but hospital B has a different PACS than hospital A, the viewer 120 can stream image(s) from the remote EA 150 at hospital B to read locally at hospital A. The workflow manager 110 accesses the exam via the archive 150 at hospital B but views, annotates, etc., via the viewer 120 at hospital A. Hospital B retains ownership of the exam, and the local viewer 120 at hospital A has not made a copy of the exam but can view, modify, annotate, report, etc., remotely via the archive 150 at hospital B. Rather, the viewer 120 at hospital A and another system at hospital B can both work on the same copy of the exam stored in the EA 150 to reduce errors, avoid loss of annotation, eliminate duplicate records, etc.

Figure 2:
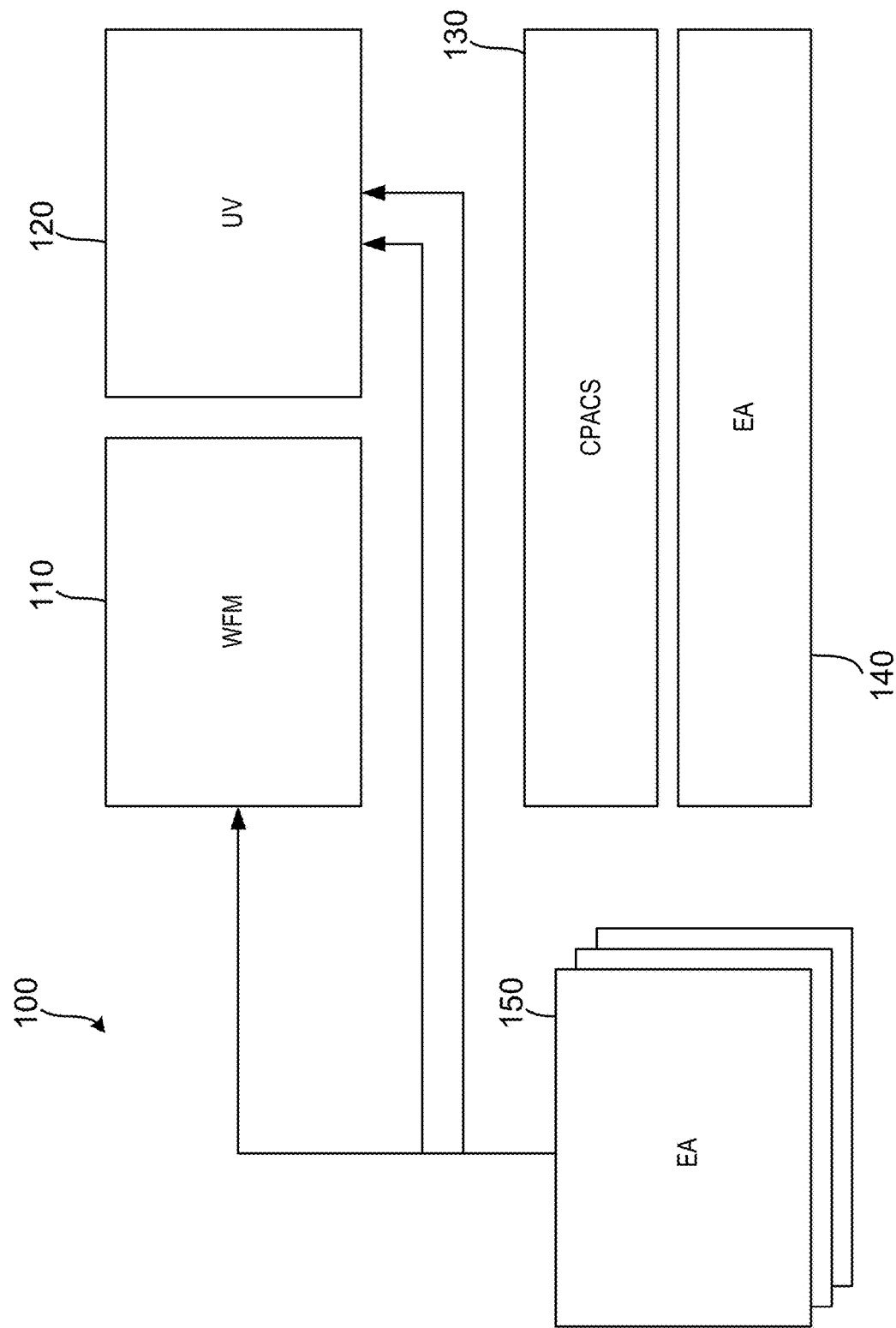

FIG. 2 illustrates the example system 100 in which a remote primary exam is to be read at a local site along with a comparison between exams (e.g., remote and remote, etc.). As shown in the example of FIG. 2, the local site includes the workflow manager 110, the diagnostic viewer 120, the PACS 130, and the EA 140. The remote site includes another EA 150. The workflow manager 110 can search the remote archive(s) 150 by patient demographic, study detail, etc., to retrieve an image/exam for display and interaction via the local viewer 120, for example. The primary study from the remote EA 150 can be launched in the viewer 120 directly from the remote archive(s) 150. Searching and streaming can be provided to the local viewer 120 from multiple remote archives 150, for example. Additionally, remote comparisons of images, exams, etc., can be hung together at the local viewer 120 by retrieving and displaying the images/exams at the local viewer 120 according to local viewer 120 preferences, hanging protocol, smart reading protocol, etc.

For example, if a patient has never been to hospital A, only hospital B, but is now at hospital A, the workflow manager 110 can provide the viewer 120 with exams and history from the remote archive(s) 150 at hospital B and hang them together for comparison exam via the viewer 120 at hospital A.

Figure 3:
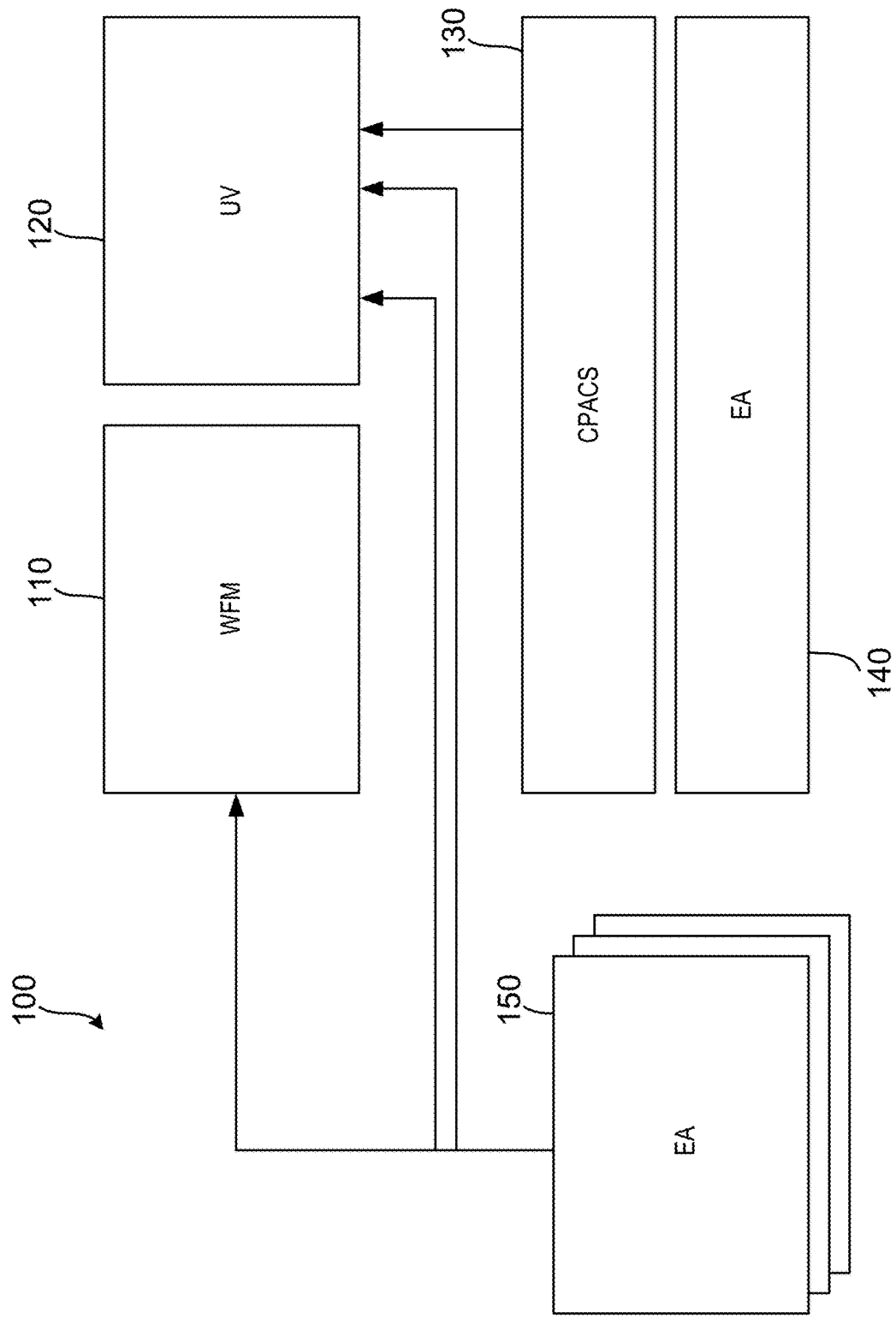

FIG. 3 illustrates the example system 100 in which a remote primary exam is to be read at a local site along with a comparison between exams (e.g., local and remote, remote and remote, etc.). As shown in the example of FIG. 3, the local site includes the workflow manager 110, the diagnostic viewer 120, the PACS 130, and the EA 140. The remote site includes another EA 150. The workflow manager 110 can search the remote archive(s) 150 by patient demographic, study detail, etc., to retrieve an image/exam for display and interaction via the local viewer 120, for example. The primary study from the remote EA 150 or the local EA 140 can be launched in the viewer 120 directly from the remote archive(s) 150. Searching and streaming can be provided to the local viewer 120 from multiple remote archives 150, for example. Additionally, comparisons of both local and remote images, exams, etc., can be hung together at the local viewer 120 by retrieving and displaying the images/exams at the local viewer 120 according to local viewer 120 preferences, hanging protocol, smart reading protocol, etc. Comparisons can be provided from the local EA 140 and the remote EA 150 for hanging and analysis, for example.

For example, if a patient was seen at hospital A with a first identifier and at hospital B with a second identifier, the workflow manager 110 can match the first and second identifiers to the same patient (e.g., using patient identifying information such as name, address, social security number, physiological data, patterns of data, etc.) and retrieve and hang all related data, both local 140 and remote 150, at the viewer 120 for analysis at hospital A (or remote from home/travel, etc.).

Figure 4:
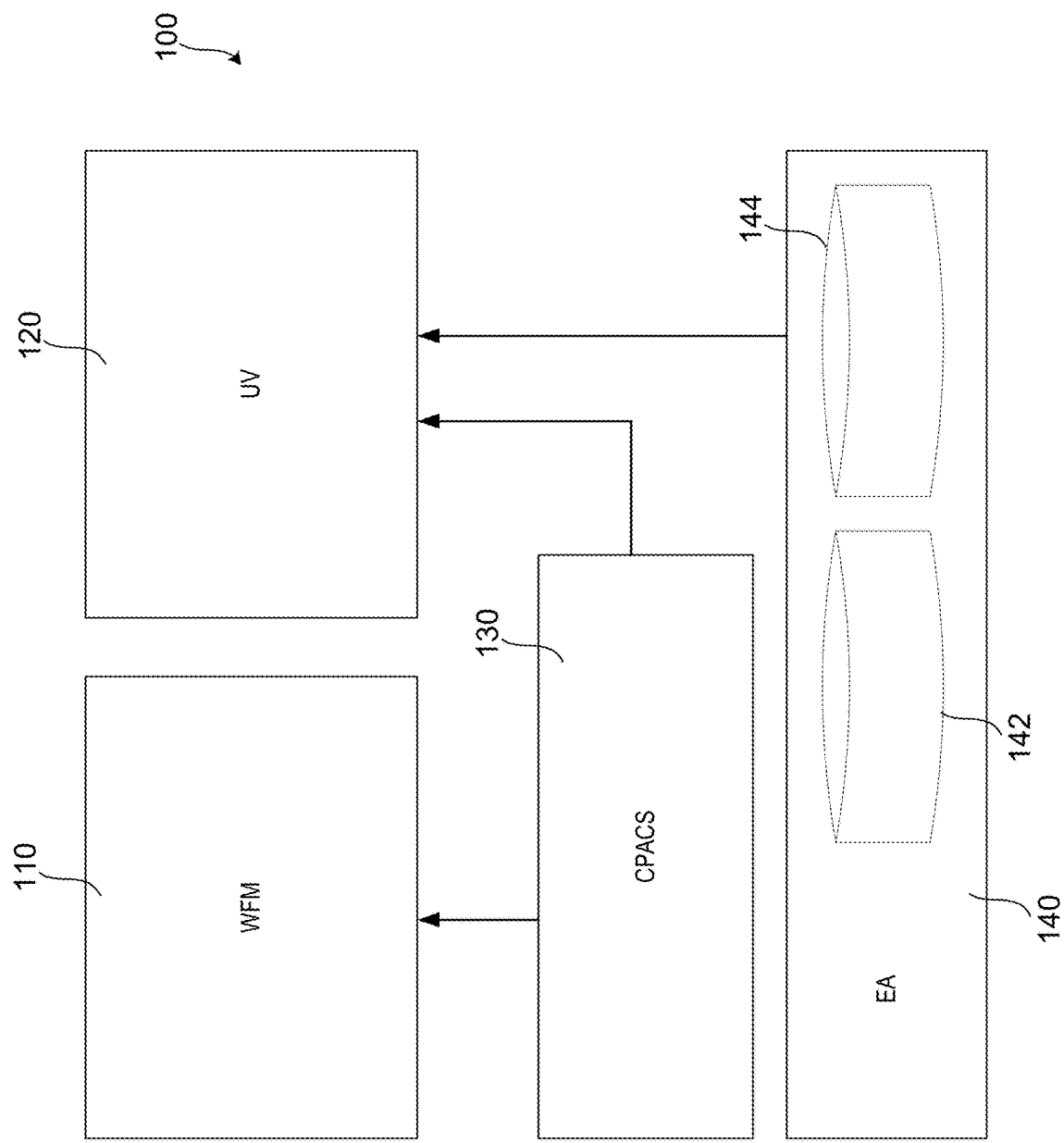

FIG. 4 illustrates the example system 100 in which a local primary exam is read and compared to exams from other departments, systems, etc., in the same enterprise/facility. As shown in the example of FIG. 4, the local site includes the workflow manager 110, the diagnostic viewer 120, the PACS 130, and the EA 140. The EA 140 includes multiple data stores 142, 144 associated with different departments, systems, etc. The workflow manager 110 can search the EA 140 and its data stores 142, 144 to retrieve and consolidate patient information, hang and read comparisons, etc., for display and interaction via the local viewer 120, for example. As such, information from different systems can be consolidated to provide a more unified view of a patient's history via the local viewer 120, for example. Information from the PACS 130 and one or more data stores 142, 144 of the EA 140 can be coordinated, streamed, and hung for display and interaction via the local viewer 120. For example, exams from radiology, cardiology, etc., for the same patient can be brought together and viewed as a single patient record (e.g., a single patient "jacket") via the viewer 120.

Figure 5:
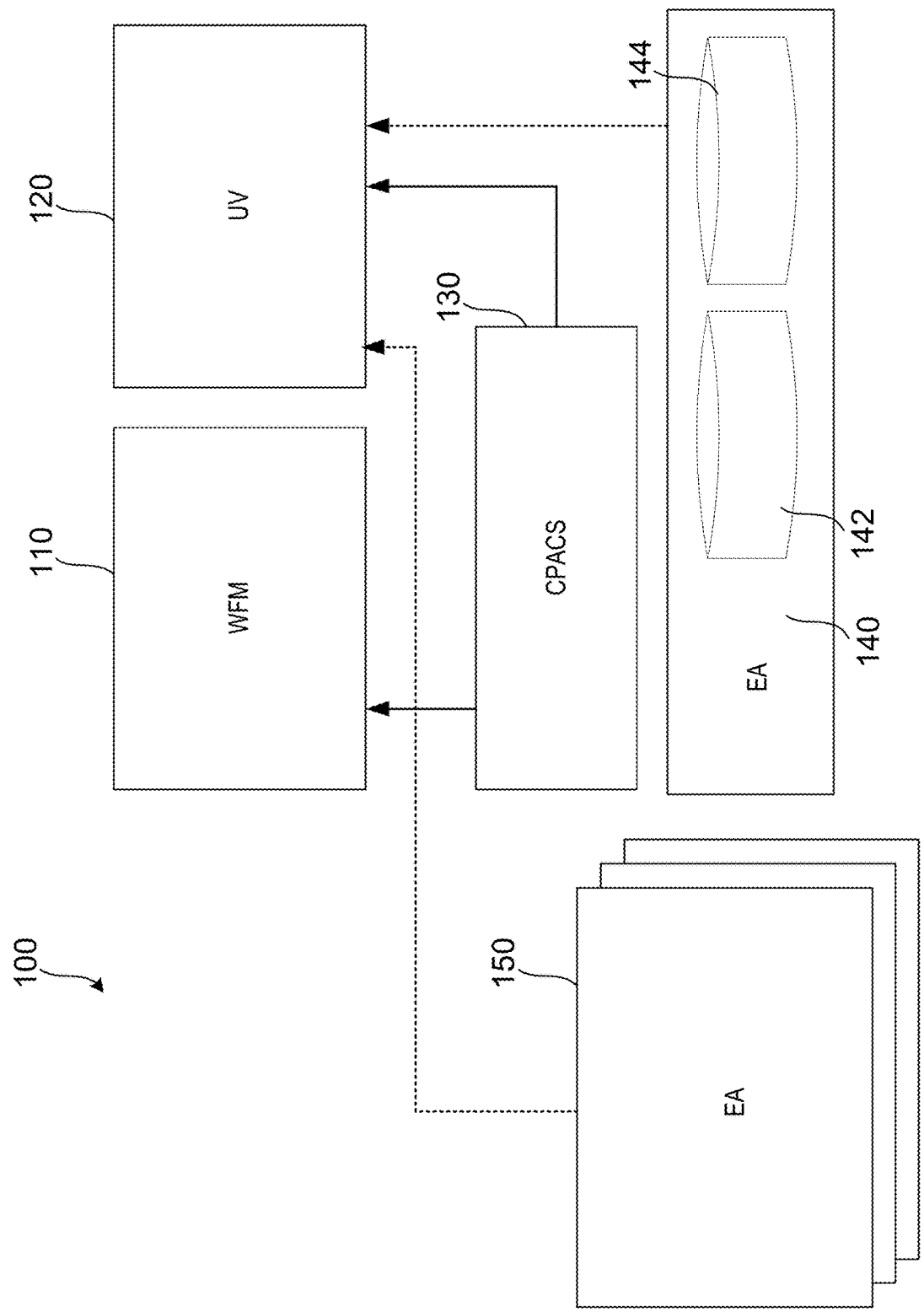

The example of FIG. 5 is similar to that of FIG. 4 with the addition of information from the remote EA 150 as well as local sources 130, 140, etc. FIG. 5 illustrates the example system 100 in which a local primary exam is read and compared to exams from other departments, systems, etc., in the same enterprise/facility and in a different enterprise, facility, etc. As shown in the example of FIG. 5, the local site includes the workflow manager 110, the diagnostic viewer 120, the PACS 130, and the EA 140. The EA 140 includes multiple data stores 142, 144 associated with different departments, systems, etc. The example system 100 also includes the remote EA 150. The workflow manager 110 can search the EA 140 and its data stores 142, 144 to retrieve and consolidate patient information, hang and read comparisons, etc., for display and interaction via the local viewer 120, for example. The viewer 120 can also access the remote archive(s) 150 to provide additional information for comparison. As such, information from different systems can be consolidated to provide a more unified view of a patient's history via the local viewer 120, for example. Information from the PACS 130 and one or more data stores 142, 144 of the EA 140 and/or the EA 150 can be coordinated, streamed, and hung for display and interaction via the local viewer 120. For example, exams from radiology, cardiology, etc., for the same patient at one or more hospitals can be brought together and viewed as a single patient record (e.g., a single patient "jacket") via the viewer 120.

Figure 6:
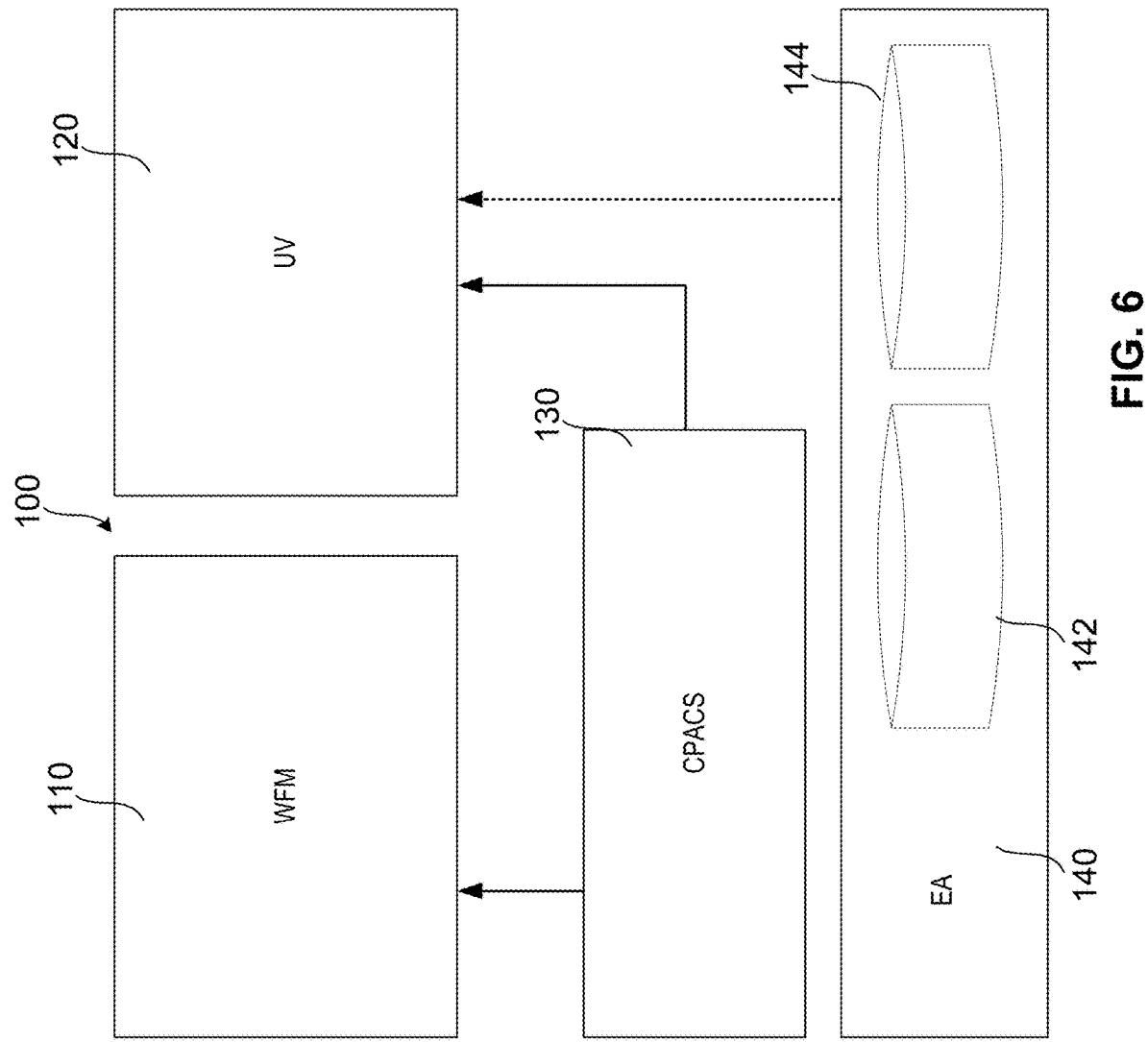

FIG. 6 provides an example of information being migrated from one system to another (e.g., from an old PACS to a new PACS, etc.). In the example of FIG. 6, data from both the old system and new system is available via the local viewer 120. New patients can be processed through the new system while old patients remain in the old system. However, access to older data is available without migration (e.g., since the migration process can take a few years).

FIG. 6 illustrates the example system 100 in which orders and patient history are migrated to the PACS 130 and pixels (e.g., images) are migrated to the EA 140. As shown in the example of FIG. 6, the local site includes the workflow manager 110, the diagnostic viewer 120, the PACS 130, and the EA 140. The EA 140 includes multiple data stores 142, 146, with data store 146 associated with migrating data from another/older system or source, for example. The workflow manager 110 can search the EA 140 and its data stores 142, 146 to retrieve and consolidate patient information, hang and read comparisons, etc., for display and interaction via the local viewer 120, for example. As such, information from different systems can be consolidated to provide a more unified view of a patient's history via the local viewer 120, for example. Information from the PACS 130 and one or more data stores 142, 144 of the EA 140 can be coordinated, streamed, and hung for display and interaction via the local viewer 120 as a single patient record (e.g., a single patient "jacket"), for example.

Figure 7A:
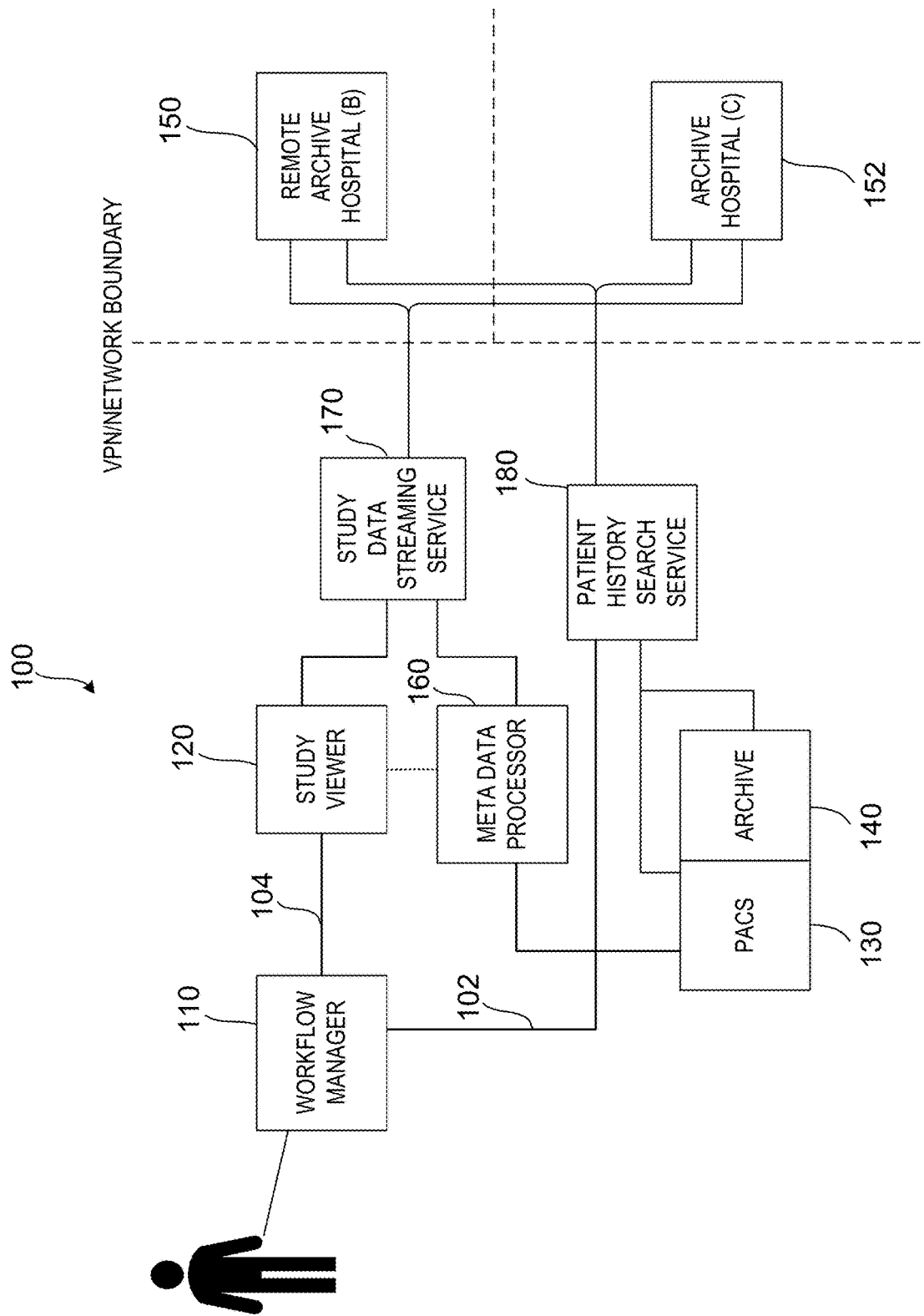
FIGS. 7A-7B illustrate an example system and associated process to search and stream information from multiple systems for review via a local viewer.

FIG. 7A illustrates an example implementation of the system 100 and associated method or process to search and stream information from multiple systems for review via a local viewer. As shown in the example of FIG. 7A, a user uses the workflow manager 110 to perform a patient history search. In certain examples, the workflow manager 110 initiates a search based on patient history and identifies exams that are available for a particular patient. The system 100 searches data across enterprises and returns study information. A user can then launch a particular study and view study information via a study viewer 120.

As shown at 102 in the example of FIG. 7A, the workflow manager 110 requests a search for a patient via a patient history search service 180, which communicates with one or more remote archives 150, 152 as well as local sources (e.g., a picture archiving and communication system (PACS) 130, an image archive 140, etc.) to retrieve and organize relevant patient search results. The patient history search service 180 provides a list of studies with location and identity information, for example. Content can be retrieved by a study data streaming service 170 based on information provided by the patient history search service 180, for example.

As shown at 104 in the example of FIG. 7A, the workflow manager 110 can launch a study via the study viewer 120 (e.g., based on user selection, based on a schedule, based on a trigger due to upcoming patient appointment, procedure, etc.). At study launch, a meta data processor 160 collects meta data from one or more locations, archives, etc. For example, the meta data processor 160 can gather meta data from local sources such as the PACS 130, archive 140, etc., and can trigger the study data streaming service 170 to gather meta data from remote sources 150, 152, for example. The study data streaming service 170 also provides pixel data to the viewer 120 from one or more remote sources 150, 152, for example. The image pixel data and associated meta data can be formatted by the viewer 120 for image display and interaction via one or more settings, protocols, preferences, etc.

Thus, for example, the meta data processor 160 is asked (e.g., triggered by the study viewer 120, etc.) to retrieve metadata from a remote location (e.g., hospital B) 150. The meta data receiver in 170 connects to the remote archive at hospital B 150 and requests further details for that specific study (e.g., study information, series information, image information, location details (e.g., archive, device, etc.), etc.). The study data streaming service 170 relays this request and provides results meta data to the meta data processor 160 and for display back to the study viewer 120. The study viewer 120 uses location information from the meta data and can prioritize display, layout, configuration, etc., based on a hanging protocol to be applied, other preference, etc. The study viewer 120 triggers the study data streaming service 170 (e.g., a pixel service, etc.) to retrieve an image from a source 150, 152. In certain examples, the service 170 decodes a token to determine from which archive 150, 152 the image is to be retrieved and how to retrieve the image/study. The study viewer 120 knows which token(s) are to be passed to retrieve the information quickly and display the information properly on the viewer 120, for example.

In certain examples, if a requested image study is divided across multiple archives 150-152, the study data streaming service 170 retrieves information from the multiple archives 150-152. The service 170 and the viewer 120 are aware of the distribution of study images from the search completed by the patient history search service (provided to the workflow manager 110 to impact selection and operation of the study viewer 120, for example). In certain examples, the study data streaming service 170 and/or the study viewer 120 can filter retrieved data to avoid duplicate information provided for display via the viewer 120. If a study, exam, etc., has elements in the remote archive of hospital B 150 and the archive of hospital C 152, the study viewer 120 can utilize meta data in associated tokens to retrieve the elements from both archives 150, 152.

A token is a portion of data that can be passed from one system to another system and provide a query, an instruction, an update, etc., between the systems. For example, a token can be used to provide an indication of a patient, a study, authentication and/or authorization to request an image/study, etc. By packaging and a query or request into one or more tokens and sending those token(s) across a network boundary, the archive and/or other remote system 150, 152 on the other side of that boundary can understand the request, identify the associated information, determine whether the requester is authorized to receive that information, and transmit the requested information and/or access to that information (e.g., remotely via a link or pointer to the file(s) at the source 150, 152) back across the network boundary to the study service 170.

Figure 7B:
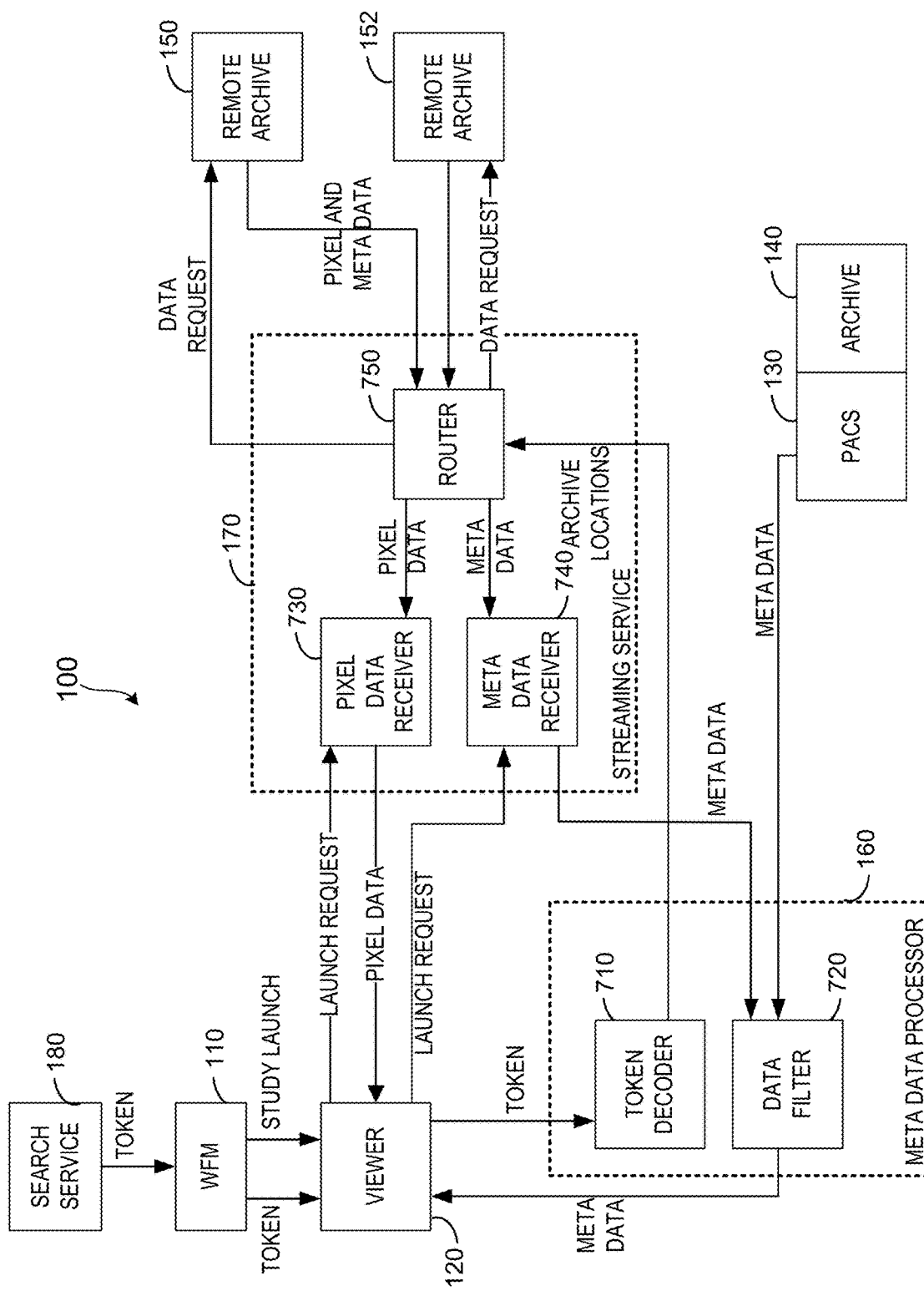
Figure 8:
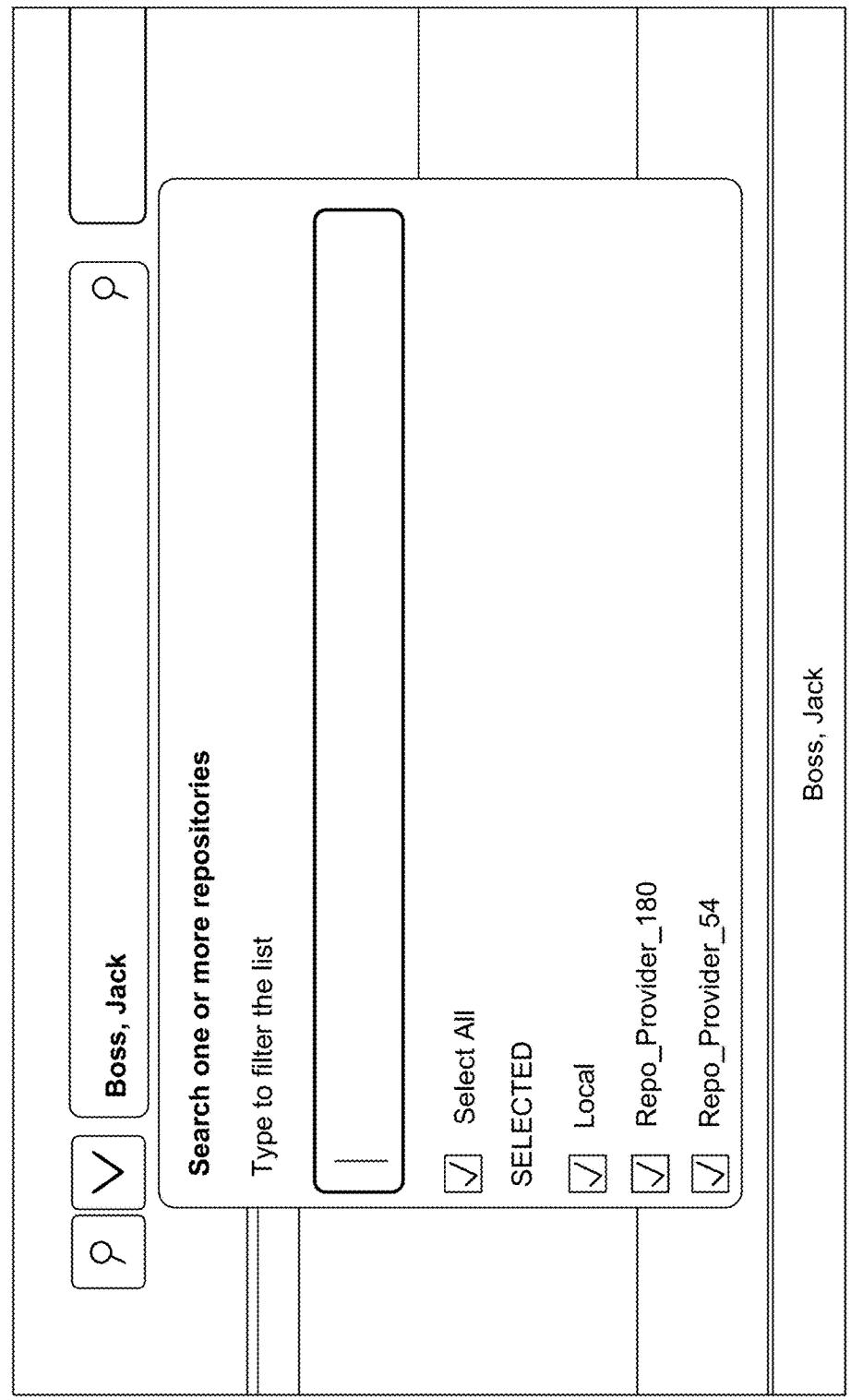

FIG. 7B illustrates an example implementation of the system 100 of FIG. 7A. As shown in the example of FIG. 7B, the example meta data processor 160 includes a token decoder 710 and a data filter 720. The example streaming service 170 of FIG. 7B includes a pixel data receiver 730, a meta data receiver 740, and a router 750. As shown in the example of FIG. 7B, the study search service 180 generates a token based on patient image search results retrieved from the one or more information sources 130, 140, 150, 152. The workflow manager 110 receives that token to retrieve image(s) for a particular patient/patient study and uses the token along with a request to launch a study sent to the study viewer 120.

The study viewer 120 provides a launch request to the streaming service 170. The study viewer 120 also provides the token to the token decoder 710 of the meta data processor 160. The token decoder 710 converts the search token generated by the search service 180 into one or more archive location(s) 150-152 for the router 750 of the streaming service 170. The router 750 uses the archive location(s) 150-152 from the token provided by the token decoder 710 to form one or more data requests to retrieve data and/or open a connection to stream image and/or other data from the archive(s) 150-152, for example. Based on prior analysis and processing of meta data by the data filter 720, location(s) 130, 140, 150-152 storing relevant content have been identified and used to formulate the token.

The remote archive(s) 150, 152 process the request(s) and respond with pixel and meta data. In certain examples, a verification of user/requester identification (e.g., authentication), authorization to access requested content, etc., can be conducted by the router 750 and/or by the archive(s) 150-152 to help ensure that content is streamed to a valid recipient entitled to view and/or modify the content. Such authentication and/or authorization can occur based on information included in the token, data request, associated profile, etc. The router 750 of the streaming service 170 receives the pixel data and meta data and routes the pixel data to the pixel data receiver 730 and the meta data to the meta data receiver 740.

The pixel data receiver 730 receives pixel data from the router 750 (e.g., a stream of pixel and/or voxel data received from one or more of the remote data sources 150-152, etc.). The pixel data receiver 730 can process the received data to filter the data, clean the data, use the data for machine learning network testing and/or training, apply a preference of setting (e.g., contrast, brightness, window level, and/or other adjustment) to the data, etc. The image data can then be provided to the study viewer 120 for display, for example.

The meta data receiver 740 receives meta data from the router 750. The meta data receiver 740 can process the received meta data to identify the associated image information, match the image to a patient, study, location, etc., and/or other correlation/configuration, for example. The meta data receiver 740 can provide the meta data to the study viewer 120 to form token(s), drive a hanging protocol to display the image data, apply other preference and/or setting to display of the pixel/voxel data via the viewer 120, etc. In certain examples, the meta data provides details associated with a retrieved image study such as study information, series information, image information, location details (e.g., archive, device, etc.), etc., for the viewer 120. The viewer 120 uses location information from the meta data, for example, to prioritize image display based on hanging protocol to be applied, etc.

Thus, based on a selection and/or trigger from the workflow manager 110, as well as input from the data filter 720 of the meta data processor 160, the study viewer 120 determines which token(s) to pass to quickly retrieve (e.g., based on an information prefetch and/or dynamically determined) from one or more remote data sources 150-152. The streaming service 170 and its router 750 decodes the token(s) to determine where to locate the content and how to retrieve the content. The content can then be streamed to the viewer 120 via the service 170 and its receivers 730-740, stored locally in an archive 140, PACS 130, etc., and/or otherwise processed. In certain examples, the content is dynamically streamed from the remote source(s) 150-152. In other examples, the content is prefetched to the local data store 140 to be retrieved and displayed at another time via the viewer 120.

Figure 10:
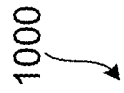
Figure 12:
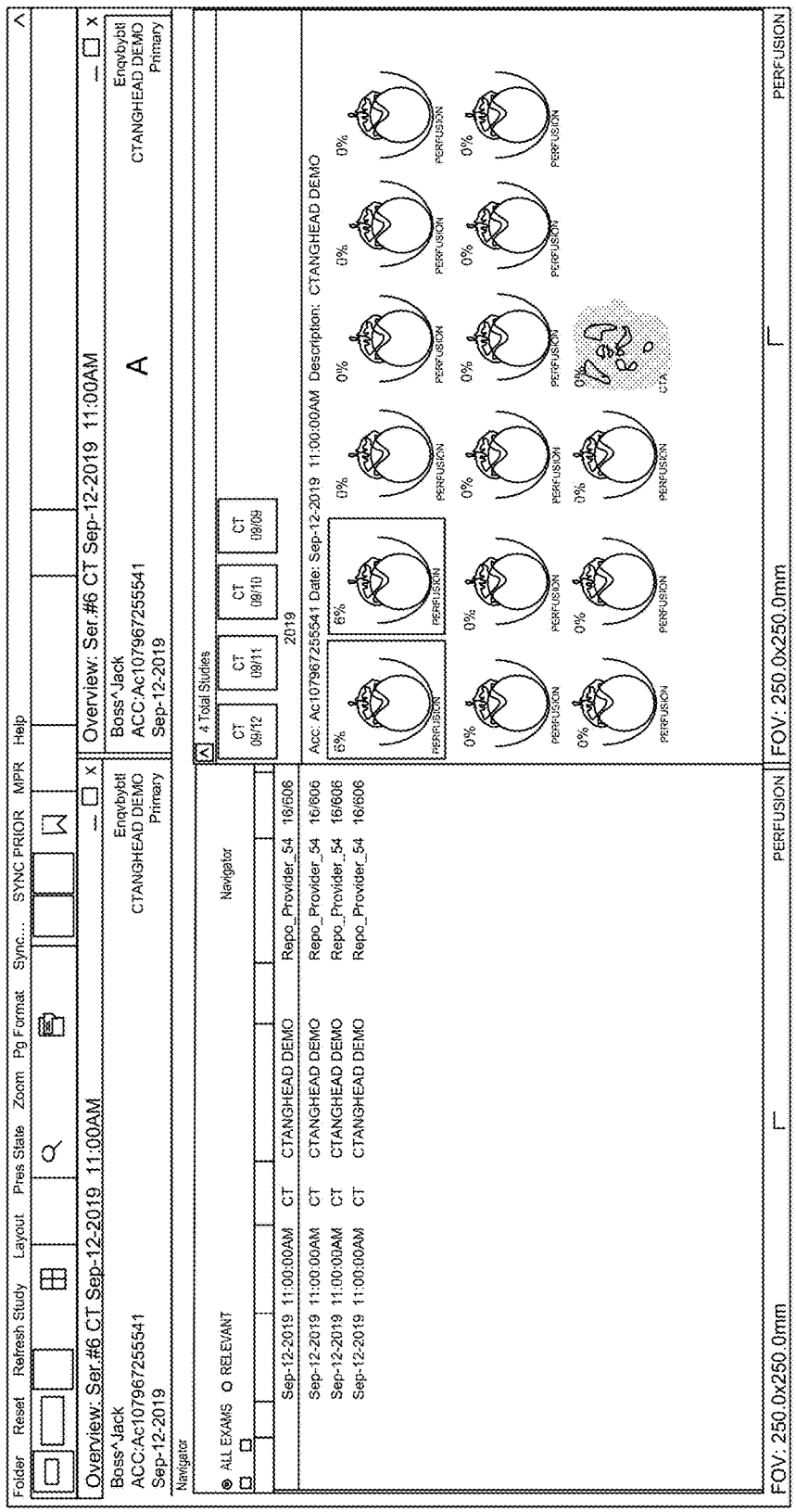

FIGS. 8-12 illustrate example graphical user interfaces 800-1200 that can be generated using the example system 100. The example interface 800 of FIG. 8 can be used to search for patient record(s) by patient demographic, study detail, etc., to access the remote archive 150. The example interface 900 of FIG. 9 illustrates an example list of study results returned from a query via the interface 800. The example interface 1000 of FIG. 10 shows example patient and study information display in a user's workflow via the workflow manager 110. The example interface 1100 of FIG. 11 shows an example viewer navigator loaded with a patient study and display with location/remote information for each study. As shown in the example of FIG. 12, retrieved image(s) is/are displayed to a user via the viewer 120 such as in the example interface 1200. As show in the example of FIG. 12, the images are retrieved from the remote system and hung according to a local hanging protocol, reading protocol, etc. As such, local preferences can be applied to view and modify remote information, for example.

Cross-enterprise services, such as cross-enterprise fabric services, can be employed to connect the local and remote systems and provide information, edits, access controls, etc. In certain examples, the local system (e.g., the workflow manager 110, the viewer 120, etc.) can authenticate an identity of a user requesting information, and the remote system can verify that the user is authorized to access, modify, etc., the requested information. As such, if the user is not authenticated, then the local system prevents that user from searching. If the user is authenticated but not authorized to access certain systems, content, etc., then the search does not return results for which the authenticated user does not have access, for example.

Figure 13:
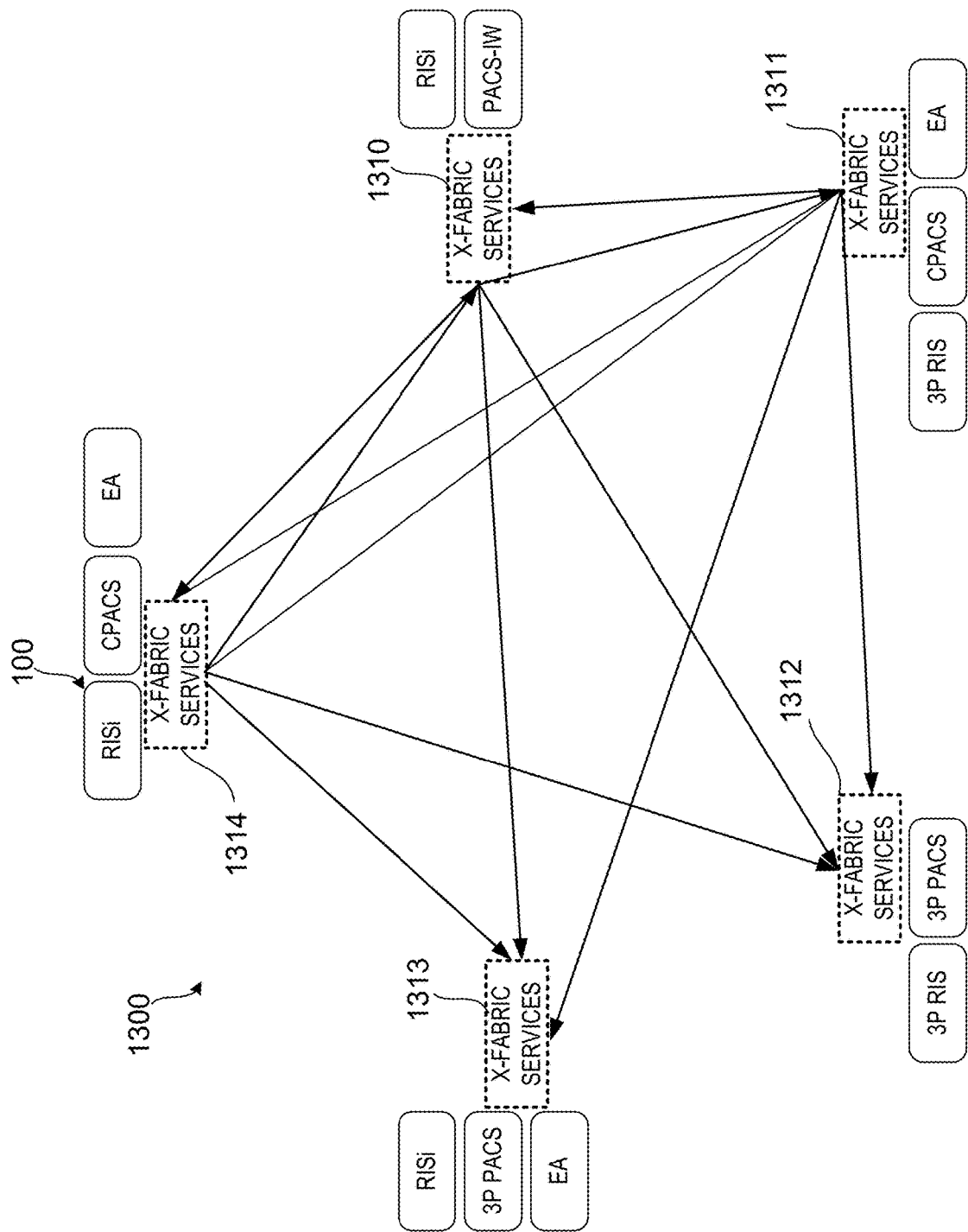
FIG. 13 is an example network configuration of multiple systems using cross-enterprise fabric services.

FIG. 13 illustrates an example network configuration 1300 in which a plurality of systems are interconnected using cross-enterprise fabric services 1310-1314. Cross-enterprise fabric services 1310-1314 enable access to data from multiple sources. In certain examples, cross-enterprise fabric services 1310-1314 include logic to process information retrieved from remote systems to help ensure that the local system (e.g., the local viewer 120) receives information in a format, style, etc., that it expects so that the local viewer 120 can process the streamed data just as it does with local data, for example.

Thus, the local viewer 120 (and its user) cannot distinguish from data provided by an external source versus data from one of its own sources. In certain examples, if a remote/external source does not have all information expected by the local viewer 120 to apply its hanging protocol, reading protocol, etc., then the viewer 120 can make the retrieved exam available in a navigator (e.g., the example navigator 1100, etc.) to allow the user to hang the exam manually, rather than automatically.

In certain examples, exams can be prioritized for comparison (e.g., by the cross-fabric services 1310-1314 and/or the workflow manager 110, etc.) based on criterion(-ia) such as body part (e.g., brain scan or chest x-ray more important than x-ray of a limb, one body part is more relevant to a particular reason for exam/patient complaint than another body part, etc.), time relevancy (e.g., an exam from three years ago is more relevant than an exam from twenty years ago, etc.), urgency, etc. Changes are made to the data at the source system, rather than at the local system, in which the viewer 120 knows nothing about the source and simply serves as a viewer/conduit for annotation and/or further action regarding the information, for example.

Using the cross-enterprise network 1300 of the example of FIG. 13, each of the cross-enterprise fabric services 1310-1314 interfaces with one or more local systems (e.g., RIS, PACS, EA, etc.) such that each enterprise can connect and interact with other participating enterprises to gather data for a patient and combine that data in presentation to a user in a single, global patient jacket/file/report via the workflow manager 110, diagnostic viewer 120, local PACS 130 and/or archive 140, etc.

In certain examples, additional privileges and/or filters can be introduced (confidential patient, anonymization, etc.) in a service layer. Privileges can be rule-based (e.g., time of day, modality type, specialty, etc.), for example, and can be tied into the unread exams list that is returned to the requesting user. Filters can be controlled by the particular enterprise that owns the order for the global reading list, for example. In certain examples, a radiology workstation can pull data from remote systems for remote exams using Web services for display via the local radiology workstation.

While the example of FIG. 13 shows a decentralized network 1300 of cross-enterprise fabric services 1310-1314, in certain examples, an alternative design uses a central "orchestrator" including automated configuration of a grid of cross-enterprise entities according to a cross-enterprise fabric manager (XFM). Worklist/jacket data can be cached using a coherence-based cross-enterprise caching appliance (XCA) in addition to an imaging cache appliance (ICA) for pre-fetch. An imaging traffic director (ITD) can be used to route to a fastest path to images (e.g., remote system, backup data center, XCA, etc.). Certain examples provide high availability, scalability, fault tolerance, application service provider model, remote archive, enhanced serviceability, etc.

In certain examples, cross-enterprise data use and data access can be separated by a "shim" layer designed to help ensure compatibility between systems, applications, etc. For example, a shim can be implemented as a library that transparently intercepts an API and changes parameters passed, handles operations, and/or redirects operations to help ensure compatibility between different systems, platforms, versions, etc.

Certain examples leverage a cross-enterprise, integrated implementation to provide a single patient jacket, which facilitates a single view of patient data across multiple imaging back ends and/or multiple enterprises. The single patient jacket enables a user participating in the cross-enterprise exchange to have a broad view of the patient through a single interface/application via the single patient jacket and integrated clinical system (e.g., rather than disconnected information and limited patient data).

A network fabric is a network topology in which components pass data to each other through interconnecting switches. The cross-enterprise fabric services 1310-1314 provide the interconnecting switches and regulating mechanism to connect systems at a plurality of sites/enterprises, for example. In certain examples, the cross-enterprise fabric services 1310-1314 form a well-defined, repeating network topology to interconnect systems and facilitate exchange of data. Using the cross-enterprise fabric services 1310-1314, traffic on the network 1300 can be divided across many available paths (e.g., as shown in the example of FIG. 13) rather than be forced onto a smaller number of more-defined paths interconnecting the systems of the network 1300. As such, data transmission can be faster and more reliable because the network fabric 1300 provides a plurality of avenues for query and response, for example.

In certain examples, the network fabric 1300 can scale as systems are added to and/or subtracted from the network 1300. Cross-enterprise fabric services 1310-1314 can be dynamically generated, configured, and deleted to accommodate systems added to or removed from the network 1300. Thus, access control can also be facilitated through the presence or absence of cross-enterprise fabric services 1310-1314 connecting systems to the network 1300, for example. Cross-enterprise fabric services 1310-1314 are software, hardware, and/or firmware constructs that connect systems to the network 1300 and enable communication, query, transmission/retrieval, etc., between systems on the network 1300, for example.

Thus, certain examples provide a unified workspace for radiologists and other clinicians combining intelligent tools, enhanced usability and access, advanced visualization, and imaging to help optimize productivity. Unlike disparate PACS and 3D systems, certain examples help to increase efficiency by simplifying information access with a single effective repository combining data from multiple sources at multiple locations including access to prior exams. In certain examples, the system (e.g., the workflow manager 110, the viewer 120, etc.) can be instantiated in a virtual environment to help organizations optimize the use of their hardware.

Healthcare organizations across the globe have an increased need to gather a patient's historical data, including exams across geographic regions or affiliated specialty care facilities. In today's complex healthcare environment, patients often seek care at multiple points of service. This may result in a patient's imaging data being stored in different DICOM sources, possibly with different patient identifiers. Cross Enterprise Display provides radiologists access to the patient's historical imaging data for comparison across affiliated organizations.

In certain examples a cross-enterprise display brings the patient's history to the viewer 120 and makes it available via a timeline, study selector, patient folder, etc. From any of these locations, the user can launch the image for side by side comparison with the primary exam. Viewer tools can be used on the remote comparison, for example. The remote images are streamed from the source, thereby avoiding the need to move images around the network and eliminating the need for complex synchronization techniques. Access to remote studies is improved by integrating a cross-enterprise network into a radiologist's existing workflows, allowing them access to view images side by side without having to launch another viewer, for example.

In certain examples, information about remote studies is integrated into the radiologists existing workflows by the workflow manager 110. Remote studies are clearly displayed within the timeline, study/series selector, navigator, viewport, and/or patient folder of the viewer 120, for example. In some examples, remote studies are indicated with an icon. In other examples, the user sees no difference between remote and local information. In some examples, when a user hovers over a tile or icon for a remote exam, the remote institution or source provider information is displayed. The institution information can be configured so that it is captured from DICOM tag or a specific name can be configured for each source, for example. In certain examples, remote comparison studies can also be saved with bookmarks and conference display protocols, for example.

In certain examples, the workflow manager 110 matches patients between a requestor and one or more providers by leveraging one of two methods. The first example method, which is less complex, leverages a single issuing authority across all the participating sites. In this method, the workload manager 110 (e.g., leveraging the cross-enterprise fabric services 1310-1314, etc.) searches each provider for an exact Patient Identifier (PID) match. If the patient has information in the remote site, the manager 110 retrieves that patient history and present it to the viewer 120.

The second example method addresses the needs of multiple sites with multiple issuing authorities. In this case, the manager 110 leverages an IRE PIX/eMPI for patient matching across the participating entities. Upon opening a local primary exam, the manager 110 makes an HL7 v2 query to an existing IHE PIX/eMPI, passing the patient ID (PID) of the local exam. If the PIX manager has other IDs for the same patient, it will respond with the corresponding mapping of PID's and Domains for the given patient. These mappings will then be forwarded to all configured providers, and, if the patient information exists in any of the providers, the workflow manager 110 retrieves the patient history for the viewer 120.

In certain examples, the example system 100 can be deployed in a centralized data center, using a federated (distributed) model, etc.

Certain examples enable viewing of images from a third-party PACS/VNA (e.g., a third-party DICOM source, etc.). Studies are streamed from the third party DICOM sources without the need to transfer the images to the local PACS 130. The remote streaming of third party images eliminates the administration effort to import and normalize external images or DVDs, for example. Third party images can be displayed via the viewer 120 without contaminating the local PACS 130 with foreign exams.

In certain examples, to display the third party image, the radiologist can click on the timeline tile. This initiates the DICOM c-move and the image is brought online and put in a viewer cache, for example. When the image is in the viewer cache, the timeline updates in real time, displaying different icons indicating the status of the move request, for example.

In certain examples, images/studies can be pre-fetched from remote sources 150-152 based on arrival of a new study in a worklist or queue to be reviewed. When the new study (e.g., an order, a scheduled exam, a performed procedure, etc.) arrives locally, a remote query can be triggered to prefetch corresponding data to be displayed via the viewer 120, for example. In certain examples, a relevancy algorithm can be applied to match patient, procedure, reason for exam, body part, image type, schedule, etc., to retrieve relevant data for display and review.

As such, content can be stored, streamed, and/or otherwise retrieved across network boundaries (e.g., across firewall, etc.) using tokens including identification information, query/request information, etc. Content can be secured and controlled by the remote archive 150-152 and still be made available for viewing, processing, and/or other usage via the study viewer 120, for example. The cross-enterprise fabric services 1310-1313 provide a data fabric to weave together data from a plurality of sources to be displayed together, processed together, etc., but retrieved and maintained separately. Internal 130, 140 and external 150, 152 data sources can be combined into a seamless interaction with patient content via the study viewer 120 (e.g., a universal viewer, zero footprint viewer, other image/data viewer, etc.). Cross-system data connections can be identified and leveraged to provide an enriched data set, improved analytics, improved data mining, collaboration, etc.

While example implementations are disclosed and described herein, processes and/or devices disclosed and described herein can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts representative of example machine readable instructions for implementing components are disclosed and described herein (e.g., in FIGS. 14-17). In the examples, the machine readable instructions include a program for execution by a processor. The program may be embodied in machine readable instructions stored on a tangible computer readable storage medium such as a CD-ROM, a floppy disk, a hard drive, a digital versatile disk (DVD), a Blu-ray disk, or a memory associated with the processor, but the entire program and/or parts thereof could alternatively be executed by a device other than the processor and/or embodied in firmware or dedicated hardware. Further, although the example program is described with reference to flowchart(s), many other methods of implementing the components disclosed and described herein may alternatively be used. For example, the order of execution of the blocks may be changed, and/or some of the blocks described may be changed, eliminated, or combined. Although the flowchart(s) depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example process(es) can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 14:
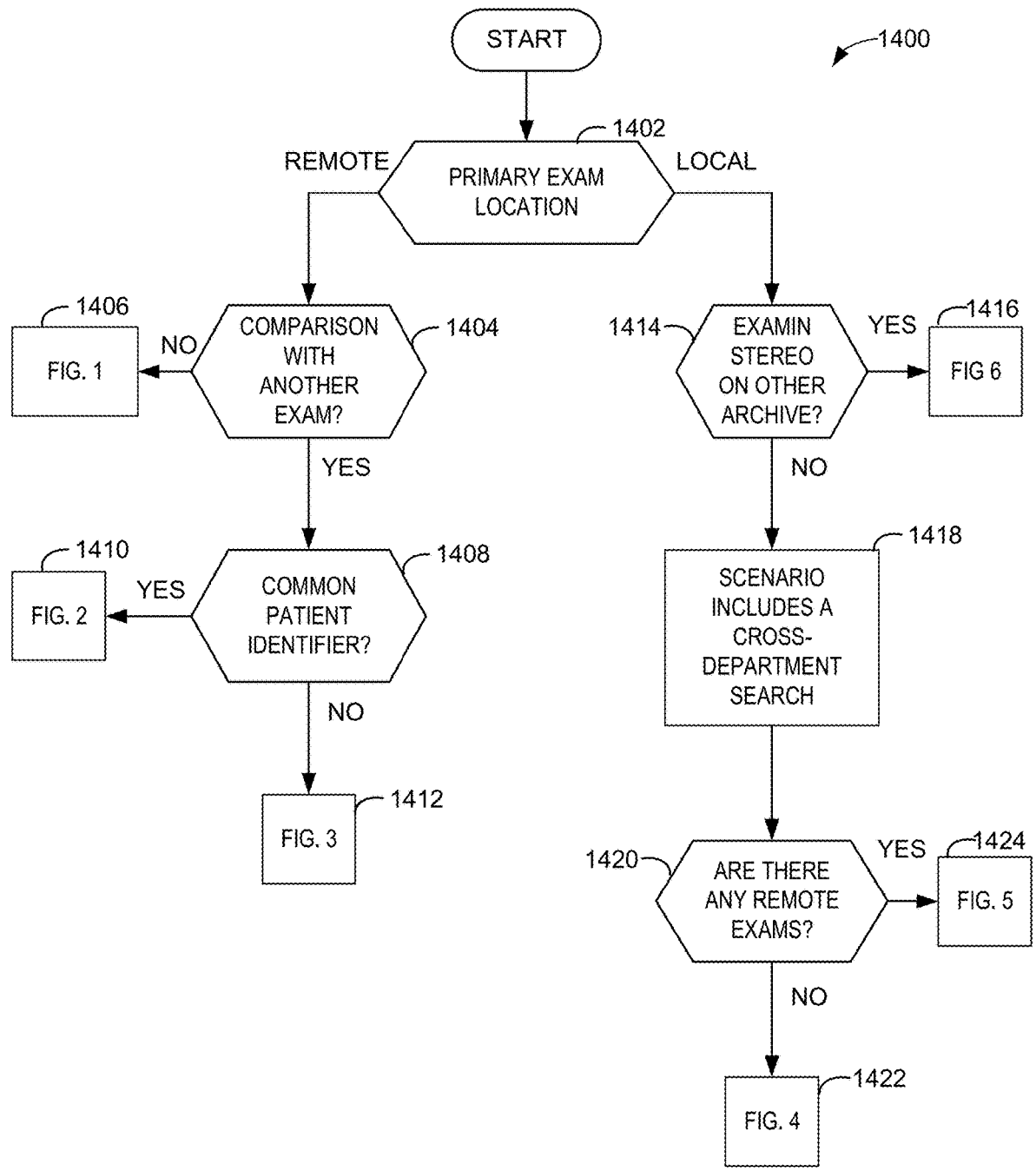
FIG. 14 is a data flow diagram showing interaction between elements of the system of the examples of FIGS. 1-7B.

FIG. 14 is a flowchart illustrating an example method 1400 to determine system 100 configuration to search for and stream patient image and/or other data. That is, the example process 1400 can be executed to determine whether the system is operating in which of the configurations described above with respect to FIGS. 1-6. The example method 1400 evaluates a primary exam to be displayed based on information associated with the exam (e.g., meta data), parameters associated with its retrieval (e.g., a selection or time-based trigger, etc., from the workflow manager 110, etc.), etc. At block 1402, a location of the primary exam is evaluated. If the primary exam is located in a remote data storage, then, at block 1404, the primary exam is evaluated to determine whether the primary exam is to be compared to another exam. If there is no comparison, at block 1406, the query for an exam and/or other image data proceeds according to the configuration of the example of FIG. 1, in which a remote primary exam is to be read at a local site. For example, the remote archive 150-152 is to be searched based on patient demographics, study details, etc., and launched in the viewer 120 directly from the remote archive(s) 150-152.

If there is to be an exam comparison, then, at block 1408, the data request is evaluated (e.g., based on meta data, token, other patient information, etc.) to determine whether there is a same patient identifier. For example, the patient may be associated with the same identifier across multiple archives 150-152, or the patient may be associated with a different identifier at each archive 150, 152. If there is a common patient identifier, then, at block 1410, the query and reading of multiple comparison exams and/or other patient data proceeds according to the configuration of the example of FIG. 2. If there are multiple patient identifiers associated with the request, then the patient is identified across multiple identifiers (e.g., using patient identifying information such as name, address, social security number, physiological data, patterns of data, etc.) to retrieve and hang content according to the configuration of the example of FIG. 3. Comparison exam(s) can be remote and/or local with respect to the primary patient exam and displayed via the study viewer 120, for example. For example, a primary study is launched in the viewer 120 directly from the remote archive(s) 150-152, and comparison image(s) are hung from the remote archive(s) 150-152 and the local PACS 130 using user preference(s) such as smart reading protocol, etc.

If the primary exam to be loaded is stored locally (e.g., in the PACS 130, local archive 140, etc.), then, at block 1414, a request is evaluated to determine whether it includes a cross-departmental search. If the request does not include a cross-departmental search, then, at block 1416, the query and reading of exams proceeds according to the example configuration of FIG. 6. For example, content may have been migrated to local PACS 130, archive 140, etc., and can be locally loaded and displayed for reading and interaction.

If the request involves a cross-departmental search, then at block 1418, the request is evaluated to determine whether the search is a local cross-departmental search or a remote cross-departmental search (e.g., a cross-hospital search). If the search is a local cross-departmental search, then, at block 1420, content query and retrieval proceeds according to the example configuration of FIG. 4. For example, content is retrieved and displayed from the PACS 130 and archive 140. If the search is a remote cross-departmental search (e.g., a cross-hospital search, etc.), then, at block 1422, content query and retrieval proceeds according to the example configuration of FIG. 5. For example, comparison exams can be streamed from local 130, 140 and remote 150, 152 sources for display and interaction via the viewer 120.

Figure 15:
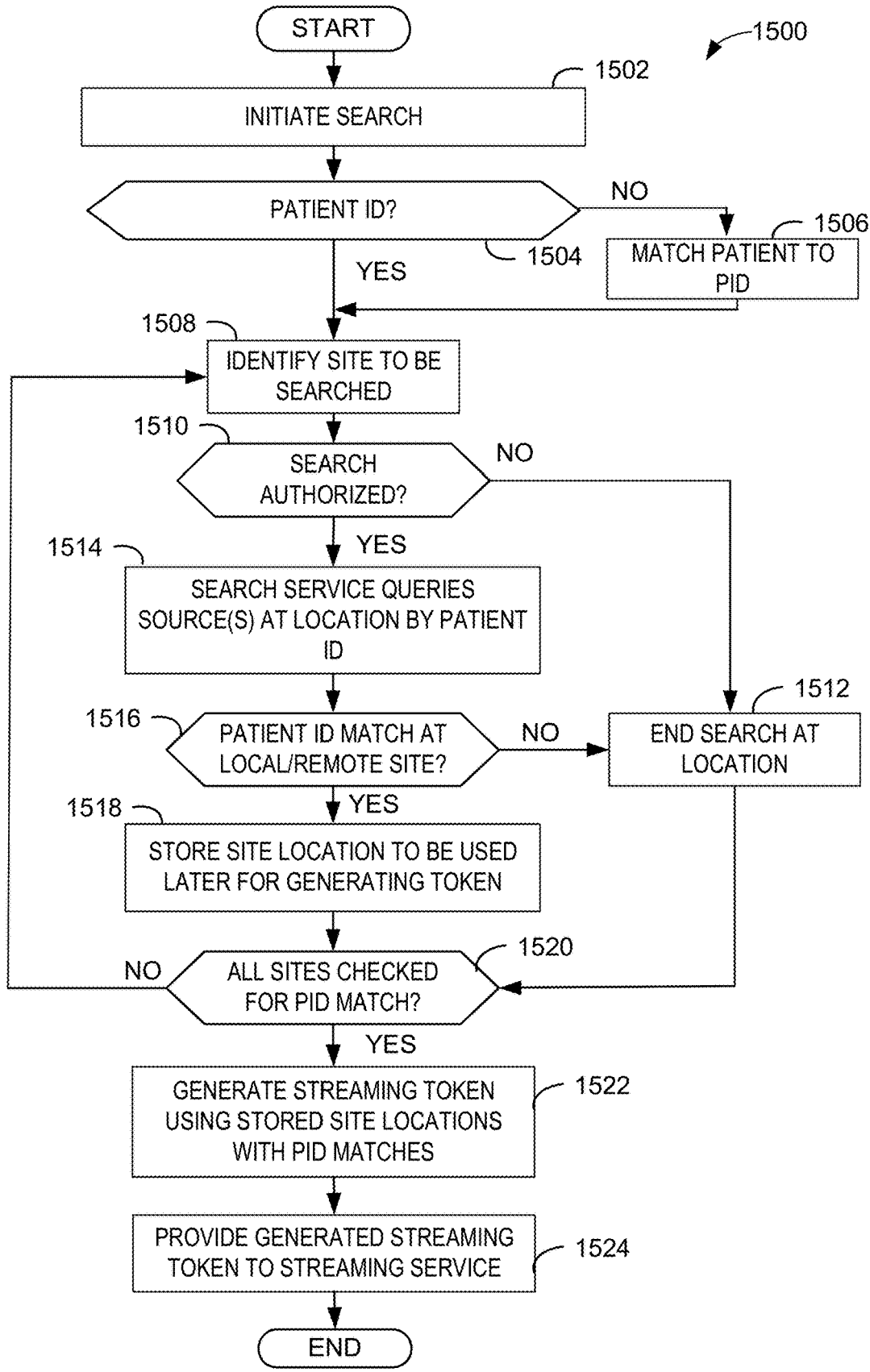
FIGS. 15-17 are flow charts of example methods of using the system of the examples of FIGS. 1-7B.

FIG. 15 is a flowchart illustrating an example method 1500 to execute a search for patient content. At block 1502, a search is initiated. For example, a user can request a study or other record for a patient via the example viewer 120, the example workflow manager 110 can automatically trigger a request to identify and locate a patient's records based on an upcoming appointment and/or other alert, etc. The example search service 180 receives and begins processing the request.

At block 1504, the search service 180 determines whether a Patient Identification Number (Patient ID or PID) has been provided. If no PID has been provided, then, at block 1506, the search service 180 leverages patient information and a database such as a Patient Identifier Cross Referencing (PIX) Integration Profile, enterprise master patient index (eMPI), etc., to match the patient to a PID using personal information such as first name, last name, social security number, etc. Once the search service 180 has determined a PID for the patient, at block 1508, the search service 180 identifies a location, system, or site (e.g., remote archive 150, 152, etc.) to query for information related to the identified patient (e.g., a patient exam, patient study, image data, etc.). For example, the remote archive 150, 152 and/or local source 130, 140 is identified for searching with respect to the patient.

At block 1510, the search/request is evaluated to determine whether the search of the site is authorized. For example, the requestor's credentials (e.g., identity, role, insurance, contract, other agreement, etc.) are evaluated to determine whether the requesting service 180, requesting user, and/or other requesting entity is authorized to search the location 130, 140, 150, 152. If the requestor is not authorized to search the location 130, 140, 150, 152, then, at block 1512, the search ends at the current site.

If the requestor is authorized to search, then, at block 1514, the search service 180 queries the data source at the location 130, 140, 150, 152 based on the PID and, at block 1516, evaluates whether the PID matches a record at the location 130, 140, 150, 152. If there is a matching PID with a study at the site, then, at block 1518, the search service 180 stores the site location 130, 140, 150, 152 to be used to generate a streaming token. If there is no match, then, at block 1512, the service 180 ends the search at the current location.

At block 1520, the search service 180 checks whether all locations connected to the system 100 via the cross-enterprise fabric 1300 have been checked for a PID match. If not, then, at block 1508, a next location 130, 140, 150, 152 to be searched is identified. Once all connected locations have been searched, then, at block 1522, one or more streaming token(s) are generated using the stored locations at which the PID was matched to a patient record/study/image/exam/ etc., and access was authorized. Token(s) can be generated using the streaming service 170, the metadata processor 160, and/or the search service 180 based on the location information, patient identification, associated record/study/image/exam/etc., for example. At block 1524, the token(s) are provided to the streaming service 170 to be used to stream pixel and meta data to the study viewer 120.

Figure 16:
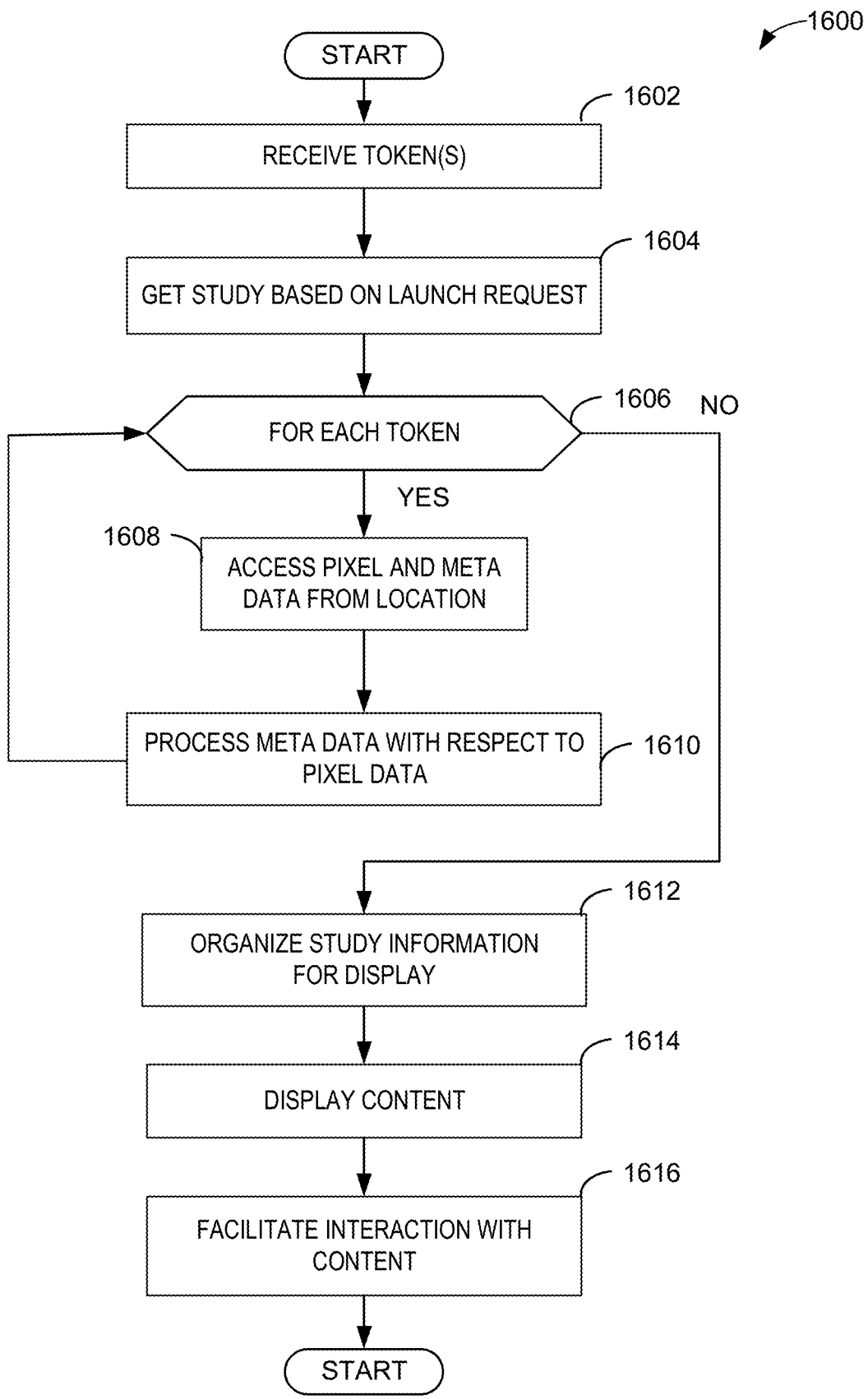

FIG. 16 is a flowchart illustrating an example method 1600 to stream pixel and meta data to a local universal viewer and/or other study viewer 120. At block 1602, the search service 180 provides one or more tokens to the streaming service 170. For example, a token corresponding to each location 130, 140, 150, 152 of patient data is provided to the router 750 of the streaming service 170. When the streaming service 170 receives a study launch request from the workflow manager 110 and/or the study viewer 120, at block 1604, study(-ies) and/or other patient content associated with the token(s) is retrieved/requested from one or more associated sources 130, 140, 150, 152. At block 1606, for each token that is relevant to the study launch request, the streaming service 170 receives pixel and meta data from a source location 130, 140, 150, 152 based on the associated token(s) (block 1608). At block 1610, the meta data is processed with respect to the pixel data. For example, the meta data receiver 740 and the pixel data receiver 730 process received meta data and pixel data to prepare the streamed content for display. The process is repeated for each relevant study and associated token.

At block 1612, retrieved study information is organized for display. For example, the retrieved content is organized by the pixel receiver 730 and the meta data receiver 740 (and/or the study viewer 120) according to a hanging protocol, meta data, other preference, etc. At block 1614, the content is displayed (e.g., streamed) via the study viewer 120. For example, the pixel data and processed meta data are streamed to the local universal viewer where a user can view, annotate, etc., the study data. At block 1616, interaction with the displayed content is facilitated via the study viewer 120. In certain examples, changes triggered/entered via the viewer 120 are made at the source location 130, 140, 150, 152.

Figure 17:
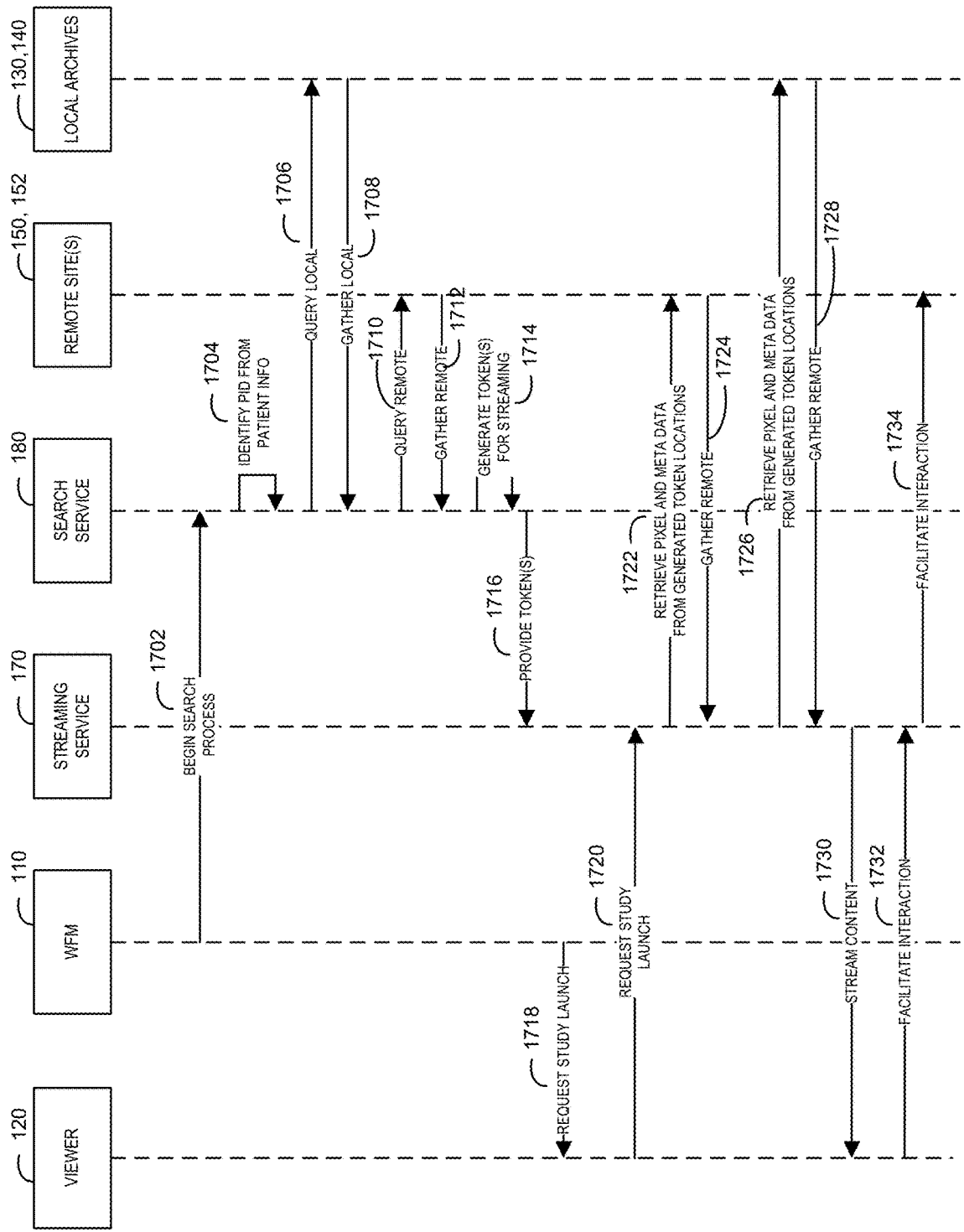

FIG. 17 illustrates an example data and instruction flow diagram 1700 involving the example system 100 to search and stream a study. At 1702, a search process begins (e.g., to query content for a patient selected via the viewer 120, to query content for a patient scheduled for an appointment, procedure, and/or other action via the workflow manager 110, to prepare for a radiology reading in a user's worklist, etc.). At 1704, the search service 180 determines a PID and/or other patient identifier from patient information available to the search service 180 (e.g., a worklist entry of the workflow manager 110, identification information from the study viewer 120, meta data from a remote source 150, 152, etc.). For example, an eMPI can be leveraged between a plurality of sources such as the local hospital A and the remote hospital B.

At 1706, the request and associated PID are used to query local data source(s) 130, 140, which, at 1708, return an indication of relevant content (e.g., corresponding to the PID and authorized for access in response to the request, etc.) to the search service 180. At 1710, the request and associated PID are used to query remote data source(s) 150, 152, which, at 1712, return an indication of relevant content (e.g., corresponding to the PID and authorized for access in response to the request, etc.) to the search service 180.

At 1714, the search service 180 generates one or more tokens to identify location(s) 130 140, 150, 152 for streaming of relevant, allowed patient content. For example, all identified locations can be combined into a single token, or an individual token can be generated for each location at which relevant, authorized patient content was identified in response to the query. In certain examples, the token(s) are generated in advance (e.g., based on a worklist, set of patient records, knowledge of upcoming exams, other meta data returned from data source(s) 130, 140, 150, 152, etc.). In certain examples, the token(s) are generated dynamically based on a request to display patient study content. The token(s) can be generated by the streaming service 170, by the meta data processor 160, by the search service 180, by the viewer 120, and/or by the workflow manager 110, for example. At 1716, the token(s) are provided to the streaming service 170.

At 1718, the workflow manager 110 sends the study viewer 120 a request to launch a patient study (e.g., based on a user selection, triggered from a worklist/schedule, etc.). At 1720, the study viewer 120 sends a request to launch the patient study to the streaming service 170. The request includes token(s) generated previously such that the search service knows where and how to gather content for the study. At 1722, 1726, the streaming service 170 retrieves the pixel and meta data from the remote site(s) 150, 152 and/or the local archives 130, 140 using the generated token(s) generated by the search service 180. At 1724, 1728, the retrieved meta data and pixel data are provided to the streaming service 170.

At 1730, the streaming service 170 provides the streamed content (e.g., pixel and/or voxel data, associated meta data, etc.) to the study viewer 120 for display. At 1732, the viewer 120 facilitates interaction with the streamed data. At 1734, the streaming service 170 routes the interaction (e.g., edits, other adjustment, reporting, simulation, scheduling, etc.) to the associated source system 150, 152 (and/or 130, 140).

Figure 18:
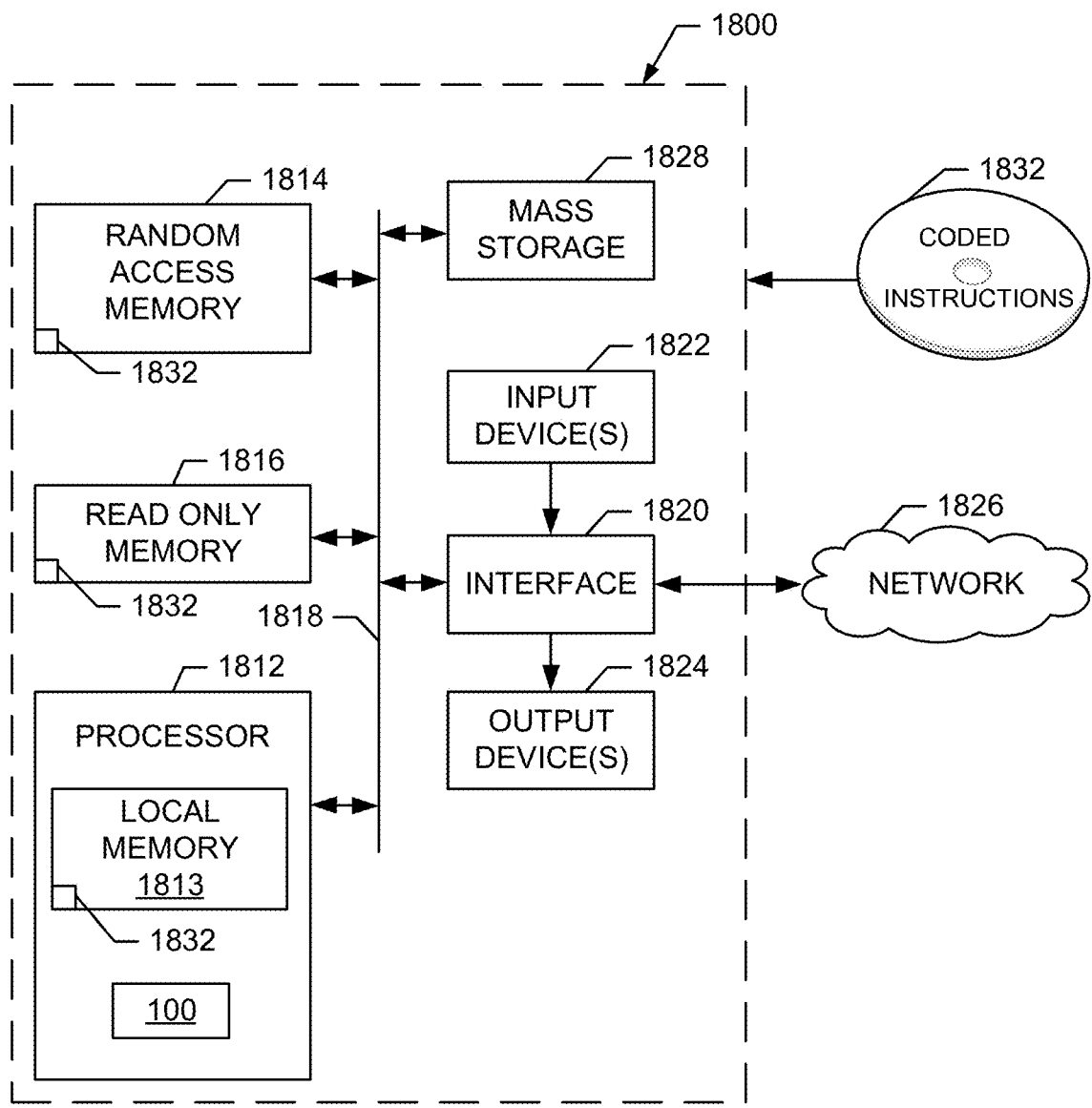
FIG. 18 is a block diagram of an example processor platform capable of executing instructions to implement the example systems and methods disclosed and described herein.

FIG. 18 is a block diagram of an example processor platform 1800 structured to execute the instructions of FIGS. 14-16 to implement, for example the example apparatus 100 of FIGS. 1-7B. The processor platform 1800 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a gaming console, a personal video recorder, a set top box, a headset or other wearable device, or any other type of computing device.

The processor platform 1800 of the illustrated example includes a processor 1812. The processor 1812 of the illustrated example is hardware. For example, the processor 1812 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 1812 implements the example apparatus 100 but can also be used to implement other systems disclosed herein.

The processor 1812 of the illustrated example includes a local memory 1813 (e.g., a cache). The processor 1812 of the illustrated example is in communication with a main memory including a volatile memory 1814 and a non-volatile memory 1816 via a bus 1818. The volatile memory 1814 may be implemented by SDRAM, DRAM, RDRAM®, and/or any other type of random access memory device. The non-volatile memory 1816 may be implemented by flash memory and/or any other desired type of memory device. Access to the main memory 1814, 1816 is controlled by a memory controller.

The processor platform 1800 of the illustrated example also includes an interface circuit 1820. The interface circuit 1820 may be implemented by any type of interface standard, such as an Ethernet interface, a USB, a Bluetooth® interface, an NFC interface, and/or a PCI express interface.

In the illustrated example, one or more input devices 1822 are connected to the interface circuit 1820. The input device(s) 1822 permit(s) a user to enter data and/or commands into the processor 1812. The input device(s) can be implemented by, for example, an audio sensor, a microphone, a camera (still or video), a keyboard, a button, a mouse, a touchscreen, a track-pad, a trackball, isopoint, and/or a voice recognition system.

One or more output devices 1824 are also connected to the interface circuit 1820 of the illustrated example. The output devices 1824 can be implemented, for example, by display devices (e.g., an LED, an OLED, an LCD, a CRT display, an IPS display, a touchscreen, etc.), a tactile output device, a printer, and/or speaker. The interface circuit 1420 of the illustrated example, thus, typically includes a graphics driver card, a graphics driver chip, and/or a graphics driver processor.

The interface circuit 1820 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1826. The communication can be via, for example, an Ethernet connection, a DSL connection, a telephone line connection, a coaxial cable system, a satellite system, a line-of-site wireless system, a cellular telephone system, etc.

The processor platform 1800 of the illustrated example also includes one or more mass storage devices 1828 for storing software and/or data. Examples of such mass storage devices 1828 include floppy disk drives, hard drive disks, compact disk drives, Blu-ray disk drives, RAID systems, and DVD drives.

The machine executable instructions 1832 of FIGS. 14-16 may be stored in the mass storage device 1828, in the volatile memory 1814, in the non-volatile memory 1816, and/or on a removable non-transitory computer readable storage medium such as a CD or DVD.

From the foregoing, it will be appreciated that example methods, apparatus and articles of manufacture have been disclosed that improve system interconnection and cross-enterprise access, control, analysis, etc., for improved system operation, improved network configuration, better data and access control, etc.

The disclosed apparatus, systems, methods, and articles of manufacture improve the efficiency and effectiveness of the processor system, memory, and other associated circuitry by leveraging cross-enterprise searching, cross-enterprise streaming, local authentication, remote authorization, remote access control and versioning, and local viewing and editing to the remote source with no persisting local copy, for example. The disclosed methods, apparatus and articles of manufacture are accordingly directed to one or more improvement(s) in the functioning of a computer and/or other processor and its associated interface. The apparatus, methods, systems, instructions, and media disclosed herein are not implementable in a human mind and are not able to be manually implemented by a human user.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus for cross-enterprise image reading, the apparatus comprising:
    a viewer at a first location to generate a request for patient content and to display at least a subset of the patient content according to a hanging protocol, the hanging protocol stored at the viewer in association with a user;
    a search service to query a plurality of sources for the patient content based on a patient identifier and a trigger associated with at least one of the user or the patient, the query to return meta data from the plurality of sources to generate at least one token stored by the search service, the at least one token encapsulating i) a second location of identified patient content at a subset of the plurality of sources and ii) an indication of access to the identified patient content at the subset of the plurality of sources; and
    a streaming service to obtain the identified patient content from the subset of the plurality of sources using the at least one token from the search service and to provide the identified patient content to the viewer for display according to the hanging protocol, the viewer in communication with the streaming service to facilitate user interaction with the subset of the plurality of sources via the displayed identified patient content, the displayed identified patient content created by reformatting, standardizing, or aggregating data provided by an external source and a local source into a single format for cross-enterprise streaming, wherein the viewer is to provide an image of the patient from the subset of the plurality of sources identified by the at least one token, wherein the image is provided side by side with other images without applying synchronization techniques to the image and without launching multiple viewer applications.

2. The apparatus of claim 1, further including a meta data processor to generate the at least one token based on meta data provided by one or more of the plurality of sources.

3. The apparatus of claim 2, wherein the meta data processor further includes a data filter to filter the meta data and a token decoder to extract location information from the at least one token.

4. The apparatus of claim 1, further including a workflow manager to organize a plurality of patients in a worklist for selection to trigger at least one of the request for patient content or the query of the plurality of sources.

5. The apparatus of claim 1, wherein the search service includes a pixel data receiver, a meta data receiver, and a router, and wherein the pixel data receiver is configured to provide pixel data to the viewer from the streaming service, the pixel data to be formatted in real-time by the viewer for image display and interaction.

6. The apparatus of claim 1, wherein the identified patient content is streamed from one or more remote archives to the viewer.

7. The apparatus of claim 1, wherein the viewer is to arrange a plurality of patient images from the identified patient content for comparison.

8. The apparatus of claim 7, wherein the plurality of patient images includes an image from a local archive and an image from a remote archive.

9. The apparatus of claim 7, wherein the plurality of patient images includes a first image from a first remote archive and a second image from a second remote archive.

10. The apparatus of claim 1, wherein the search service is to query the plurality of sources for the patient content and store the meta data to generate the one or more tokens at a first time, and wherein the streaming service is to retrieve the one or more tokens at a second time to obtain the identified patient content.

11. A computer-implemented method of cross-enterprise image reading, the method comprising:
    querying, by executing an instruction using at least one processor, a plurality of sources for patient content based on a patient identifier and a trigger associated with the patient content;

generating, by executing an instruction using the at least one processor, at least one token encapsulating i) a location of identified patient content at a subset of the plurality of sources and ii) an indication of access to the identified patient content at the subset of the plurality of sources based on meta data returned from the plurality of sources in response to the query;

obtaining, by executing an instruction using the at least one processor, the identified patient content using the at least one token;

providing, by executing an instruction using the at least one processor, the identified patient content for display and interaction via a viewer according to a hanging protocol of the viewer in response to a request, the displayed identified patient content created by reformatting, standardizing, or aggregating data provided in real-time by an external source and a local source into a single format for cross-enterprise streaming, wherein the viewer is to provide an image of the patient from the subset of the plurality of sources identified by the at least one token, wherein the image is provided side by side with other images without applying synchronization techniques to the image and without launching multiple viewer applications; and facilitating interaction with the subset of the plurality of sources via the displayed identified patient content through the viewer.

12. The method of claim 11, wherein generating the at least one token further includes filtering the meta data based on at least one criterion.

13. The method of claim 11, wherein obtaining the identified patient content includes streaming the identified patient content from one or more remote archives to the viewer.

14. The method of claim 11, further including arranging a plurality of patient images from the identified patient content for comparison.

15. The method of claim 11, further including configuring the viewer for display of a comparison among the identified patient content based on locations of at least a first source and a second source in the plurality of sources.

16. At least one non-transitory computer readable storage medium comprising instructions that, when executed, cause at least one processor to at least:

query a plurality of sources for patient content based on a patient identifier and a trigger associated with the patient content;

generate at least one token encapsulating i) a location of identified patient content at a subset of the plurality of sources and ii) an indication of access to the identified patient content at the subset of the plurality of sources based on meta data returned from the plurality of sources in response to the query;

obtain the identified patient content using the at least one token;

provide the identified patient content for display and interaction via a viewer according to a hanging protocol of the viewer in response to a request, the displayed identified patient content created by reformatting, standardizing, or aggregating data provided in real-time by an external source and a local source into a single format for cross-enterprise streaming, wherein the viewer is to provide an image of the patient from the subset of the plurality of sources identified by the at least one token, wherein the image is provided side by side with other images without applying synchronization techniques to the image and without launching multiple viewer applications; and facilitate interaction with the subset of the plurality of sources via the displayed identified patient content through the viewer.

17. The at least one non-transitory computer readable storage medium of claim 16, wherein the instructions, when executed, cause the at least one processor to generate the at least one token further by filtering the meta data based on at least one criterion.

18. The at least one non-transitory computer readable storage medium of claim 16, wherein the instructions, when executed, cause the at least one processor to obtain the identified patient content by streaming the identified patient content from one or more remote archives to the viewer.

19. The at least one non-transitory computer readable storage medium of claim 16, wherein the instructions, when executed, cause the at least one processor to arrange a plurality of patient images from the identified patient content for comparison.

20. The at least one non-transitory computer readable storage medium of claim 16, wherein the instructions, when executed, cause the at least one processor to configure the viewer for display of a comparison among the identified patient content based on locations of at least a first source and a second source in the plurality of sources.

* * * * *